(12) United States Patent
Krause

(10) Patent No.: US 10,842,535 B2
(45) Date of Patent: Nov. 24, 2020

(54) FLEXIBLE SPINE COMPONENTS HAVING MULTIPLE SLOTS

(71) Applicant: William R. Krause, Charlottesville, VA (US)

(72) Inventor: William R. Krause, Charlottesville, VA (US)

(*) Notice: Subject to any disclaimer, the term of this patent is extended or adjusted under 35 U.S.C. 154(b) by 93 days.

(21) Appl. No.: 15/799,340

(22) Filed: Oct. 31, 2017

(65) Prior Publication Data

US 2018/0049775 A1 Feb. 22, 2018

Related U.S. Application Data

(63) Continuation-in-part of application No. 14/859,670, filed on Sep. 21, 2015, now Pat. No. 9,801,663, which is a continuation-in-part of application No. 12/069,934, filed on Feb. 14, 2008, now Pat. No. 9,138,263.

(60) Provisional application No. 60/901,150, filed on Feb. 14, 2007.

(51) Int. Cl.
*A61B 17/70* (2006.01)
*A61F 2/44* (2006.01)
*A61F 2/30* (2006.01)

(52) U.S. Cl.
CPC ...... *A61B 17/7029* (2013.01); *A61B 17/7001* (2013.01); *A61B 17/7023* (2013.01); *A61B 17/7028* (2013.01); *A61B 17/7031* (2013.01); *A61F 2/44* (2013.01); *A61B 17/7041* (2013.01); *A61F 2/4425* (2013.01); *A61F 2002/3055* (2013.01); *A61F 2002/30405* (2013.01); *A61F 2002/30563* (2013.01); *A61F 2002/30566* (2013.01); *A61F 2002/30649* (2013.01); *A61F 2002/30841* (2013.01); *A61F 2310/00011* (2013.01)

(58) Field of Classification Search
CPC .................. A61B 17/7019–7031; A61B 17/70
See application file for complete search history.

(56) References Cited

U.S. PATENT DOCUMENTS

| | | | | |
|---|---|---|---|---|
| 2,515,366 A | * | 7/1950 | Zublin | ....................... E21B 7/06 138/120 |
| 3,426,364 A | | 2/1969 | Lumb | |
| 4,328,839 A | * | 5/1982 | Lyons | ..................... E21B 17/20 138/120 |
| 4,401,112 A | | 8/1983 | Rezaian | |
| 4,554,914 A | | 11/1985 | Kapp et al. | |
| 4,599,086 A | | 7/1986 | Doty | |

(Continued)

*Primary Examiner* — Eduardo C Robert
*Assistant Examiner* — Michelle C Eckman
(74) *Attorney, Agent, or Firm* — Kimberly O Snead

(57) ABSTRACT

An improved flexible component used for dynamic stabilization of spinal segments for the treatment of vertebrae deformities and injuries and for the replacement of a complete or segment of the body of a vertebra in the spine is described. The flexible component is comprised of a suitable implant material with a longitudinal bore the entire length and an appropriately formed slots that extend spirally around the flexible spinal element either continuously or segmentally. The flexible component can be encapsulated, fully or partially, in a suitable implant grade elastomeric resilient material. When used for a dynamic stabilization device, the element is attached to the vertebral bodies by pedicle screws know to those in the art.

15 Claims, 28 Drawing Sheets

(56) References Cited

U.S. PATENT DOCUMENTS

| | | | | |
|---|---|---|---|---|
| 4,600,037 | A * | 7/1986 | Hatten | F16L 11/18 138/120 |
| 4,932,975 | A | 6/1990 | Main | |
| 5,092,866 | A | 3/1992 | Breard et al. | |
| 5,147,404 | A | 9/1992 | Downey | |
| 5,192,327 | A | 3/1993 | Brantigan | |
| 5,282,863 | A | 2/1994 | Burton | |
| 5,381,782 | A * | 1/1995 | DeLaRama | A61B 1/0056 138/118 |
| 5,437,669 | A | 8/1995 | Yuan | |
| 5,474,555 | A | 12/1995 | Puno | |
| 5,488,761 | A * | 2/1996 | Leone | A61B 17/164 29/2.1 |
| 5,571,192 | A | 11/1996 | Schonhoffer | |
| 5,702,455 | A | 12/1997 | Saggar | |
| 5,776,198 | A | 7/1998 | Rabbe | |
| 6,053,922 | A * | 4/2000 | Krause | A61B 17/164 464/78 |
| 6,193,756 | B1 | 2/2001 | Studer | |
| 6,293,949 | B1 | 9/2001 | Justis | |
| 6,447,518 | B1 * | 9/2002 | Krause | A61B 17/164 606/80 |
| 6,468,276 | B1 | 10/2002 | McKay | |
| 6,645,207 | B2 | 11/2003 | Dixon | |
| 6,921,397 | B2 * | 7/2005 | Corcoran | A61M 25/0043 464/149 |
| 6,966,910 | B2 | 11/2005 | Ritland | |
| 6,986,771 | B2 * | 1/2006 | Paul | A61B 17/7023 606/254 |
| 69,891,311 | | 1/2006 | Paul | |
| 7,018,379 | B2 | 3/2006 | Drewry | |
| 7,083,621 | B2 | 8/2006 | Shaolian | |
| 7,413,563 | B2 * | 8/2008 | Corcoran | A61B 17/0057 604/523 |
| 7,621,940 | B2 * | 11/2009 | Harms | A61B 17/7026 606/257 |
| 7,766,915 | B2 * | 8/2010 | Jackson | A61B 17/7028 606/86 A |
| 8,080,038 | B2 * | 12/2011 | Bhatnagar | A61B 17/7004 606/255 |
| 8,105,368 | B2 * | 1/2012 | Jackson | A61B 17/7008 606/326 |
| 8,123,060 | B2 * | 2/2012 | Obergoenner | B65D 9/04 217/65 |
| 8,353,898 | B2 * | 1/2013 | Lutze | A61B 17/32002 606/1 |
| 8,361,118 | B2 * | 1/2013 | Biedermann | A61B 17/702 606/257 |
| 8,366,559 | B2 * | 2/2013 | Papenfuss | A61B 17/1631 464/149 |
| 8,376,865 | B2 * | 2/2013 | Forster | A61F 2/2427 464/149 |
| 8,663,284 | B2 * | 3/2014 | Beger | A61B 17/7004 606/254 |
| 8,740,944 | B2 * | 6/2014 | Trieu | A61B 17/7026 606/254 |
| 8,961,516 | B2 * | 2/2015 | Nelson | A61B 17/7233 606/64 |
| 8,974,498 | B2 * | 3/2015 | Beger | A61B 17/701 606/255 |
| 9,078,704 | B2 * | 7/2015 | Beger | A61B 17/7004 |
| 9,089,369 | B2 * | 7/2015 | Biedermann | A61B 17/705 |
| 9,399,115 | B2 * | 7/2016 | Beasley | A61M 25/0054 |
| 9,468,359 | B2 * | 10/2016 | Weisshaupt | A61B 1/00071 |
| 9,482,260 | B1 * | 11/2016 | Krause | F16B 35/041 |
| 9,532,808 | B2 * | 1/2017 | Celmerowski | A61B 17/7005 |
| 9,730,739 | B2 * | 8/2017 | Taylor | A61B 17/7208 |
| 9,775,967 | B2 * | 10/2017 | Hatta | A61B 1/0055 |
| 2002/0128715 | A1 | 9/2002 | Bryan | |
| 2003/0109880 | A1 | 6/2003 | Shirdo | |
| 2003/0220643 | A1 * | 11/2003 | Ferree | A61B 17/7023 623/17.16 |
| 2004/0236328 | A1 | 11/2004 | Paul | |
| 2004/0267260 | A1 | 12/2004 | Mack | |
| 2005/0056979 | A1 * | 3/2005 | Studer | A61B 17/7028 267/118 |
| 2005/0065516 | A1 | 3/2005 | Jahng | |
| 2005/0090898 | A1 | 4/2005 | Berry | |
| 2005/0154390 | A1 * | 7/2005 | Biedermann | A61B 17/7028 128/898 |
| 2005/0203513 | A1 | 9/2005 | Jahng | |
| 2005/0203514 | A1 | 9/2005 | Jahng | |
| 2005/0203517 | A1 * | 9/2005 | Jahng | A61B 17/7028 606/254 |
| 2005/0209694 | A1 | 9/2005 | Loeb | |
| 2005/0209697 | A1 | 9/2005 | Paponneau | |
| 2005/0261686 | A1 | 11/2005 | Paul | |
| 2005/0268581 | A1 | 12/2005 | Marnay | |
| 2006/0041259 | A1 * | 2/2006 | Paul | A61B 17/7023 606/250 |
| 2006/0184171 | A1 * | 8/2006 | Biedermann | A61B 17/7011 606/254 |
| 2006/0212033 | A1 | 9/2006 | Rothman | |
| 2006/0293755 | A1 | 12/2006 | Lindner et al. | |
| 2007/0015190 | A1 | 1/2007 | Martinez et al. | |
| 2007/0016190 | A1 * | 1/2007 | Martinez | A61B 17/7007 606/86 A |
| 2007/0016204 | A1 * | 1/2007 | Martinez | A61B 17/7059 606/279 |
| 2007/0203446 | A1 * | 8/2007 | Biedermann | A61B 17/7025 604/11 |
| 2007/0233095 | A1 * | 10/2007 | Schlaepfer | A61B 17/7031 606/279 |
| 2008/0177316 | A1 * | 7/2008 | Bergeron | A61B 17/7026 606/254 |
| 2008/0221620 | A1 * | 9/2008 | Krause | A61B 17/7028 606/255 |
| 2008/0312694 | A1 * | 12/2008 | Peterman | A61B 17/7028 606/257 |
| 2009/0036925 | A1 * | 2/2009 | Sala | A61B 17/7023 606/246 |
| 2009/0088782 | A1 * | 4/2009 | Moumene | A61B 17/7004 606/151 |
| 2009/0182378 | A1 * | 7/2009 | Choi | A61B 17/7026 606/254 |
| 2009/0270921 | A1 * | 10/2009 | Krause | A61B 17/7026 606/254 |
| 2011/0144703 | A1 * | 6/2011 | Krause | A61B 17/8625 606/309 |
| 2014/0114312 | A1 * | 4/2014 | Krause | A61B 17/8605 606/62 |
| 2017/0056979 | A1 * | 3/2017 | Krause | B23B 45/005 |
| 2018/0049775 | A1 * | 2/2018 | Krause | A61F 2/44 |
| 2018/0065235 | A1 * | 3/2018 | Krause | A61B 17/1631 |

* cited by examiner

Detail 6A

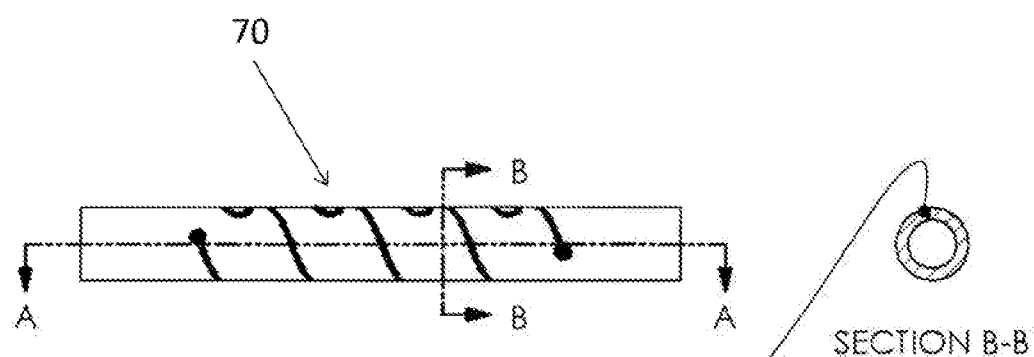
Figure 11
Figure 13 — SECTION B-B
Figure 12 — SECTION A-A

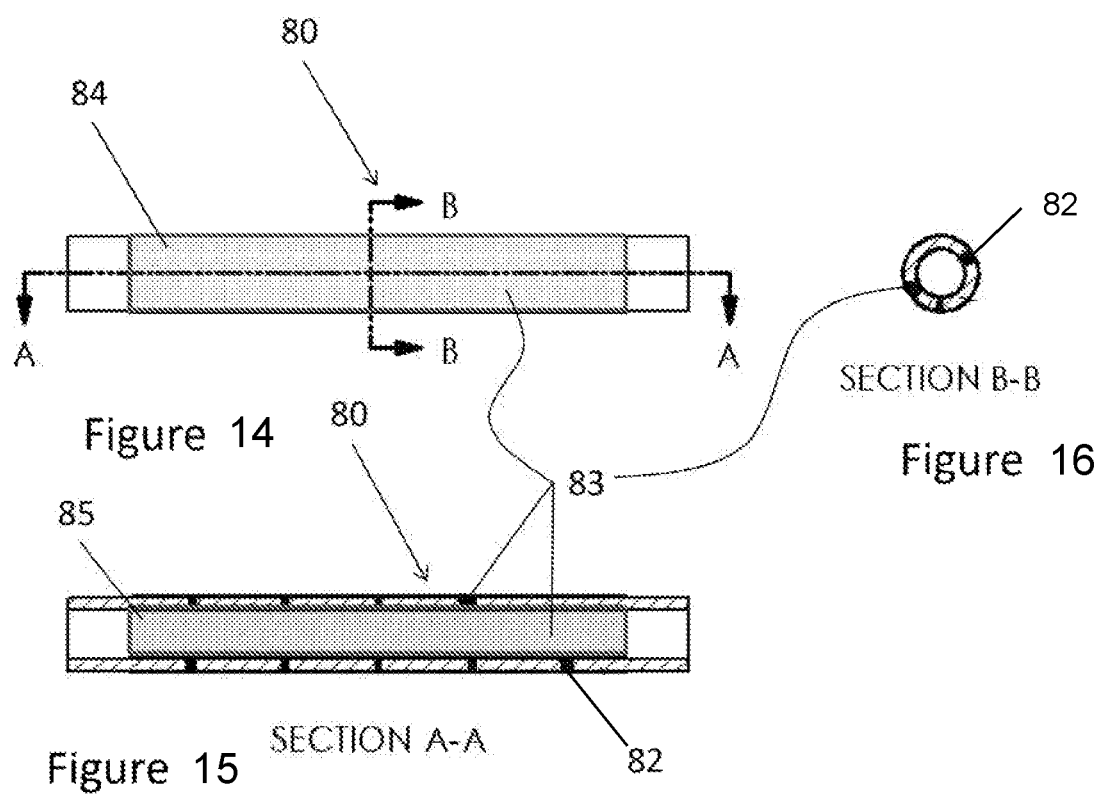

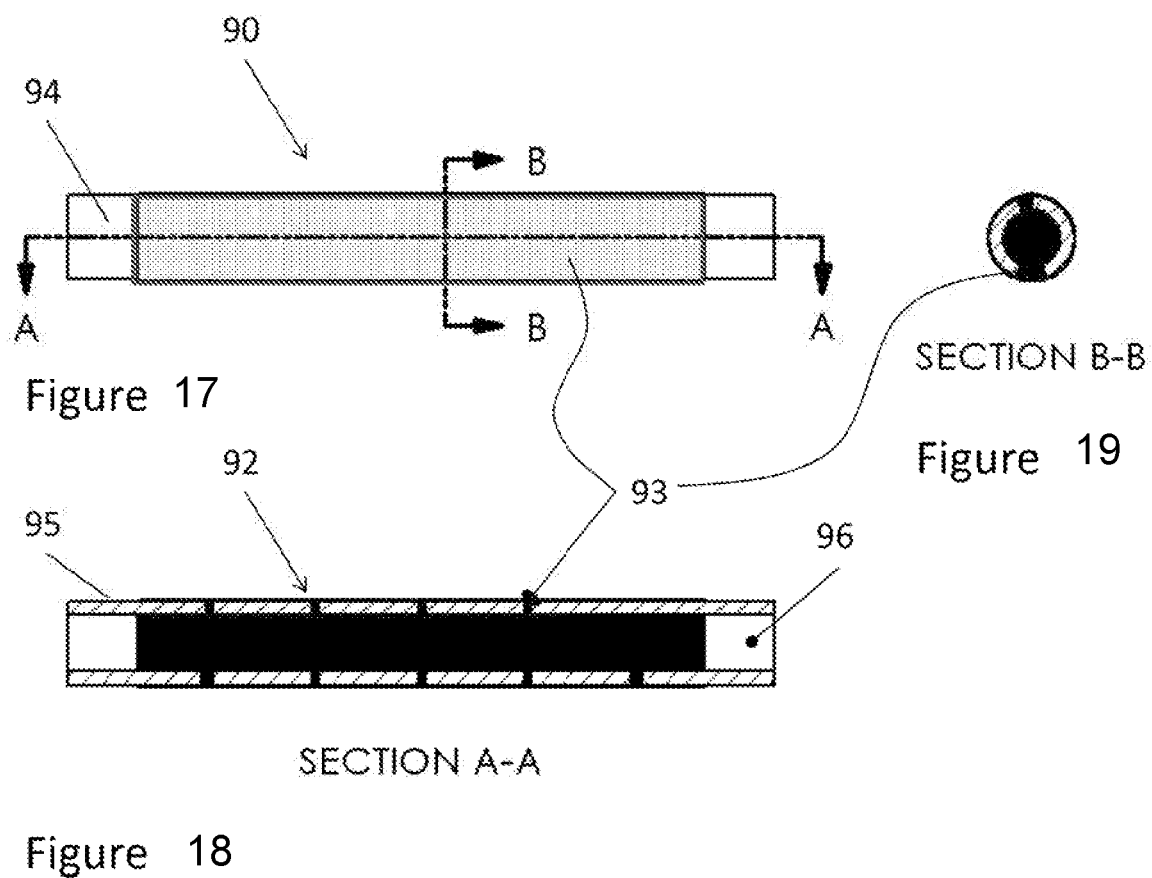

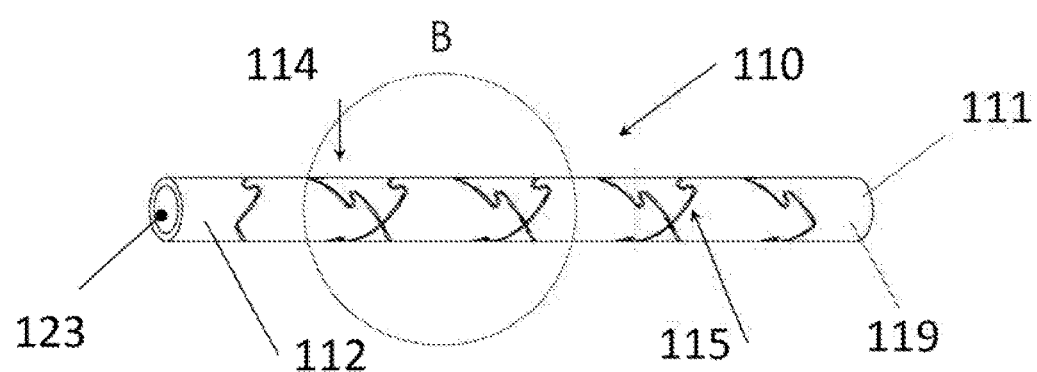
Figure 22
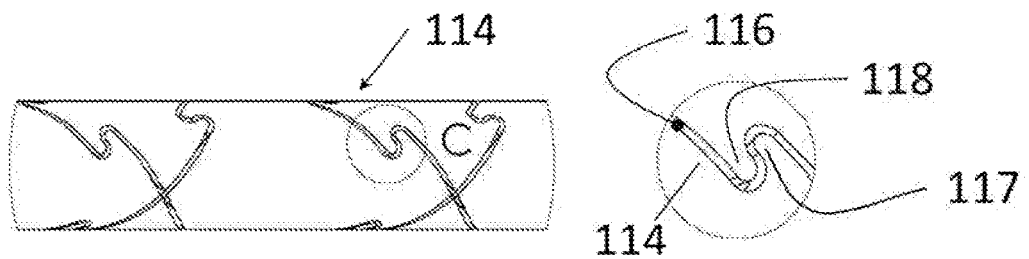
Figure 23   DETAIL B
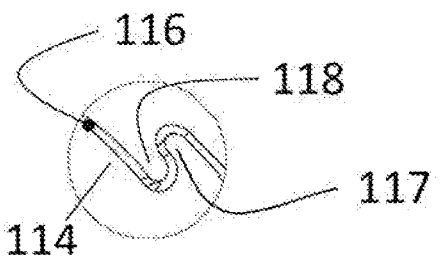
DETAIL C   Figure 24

DETAIL E

SECTION A-A

SECTION B-B

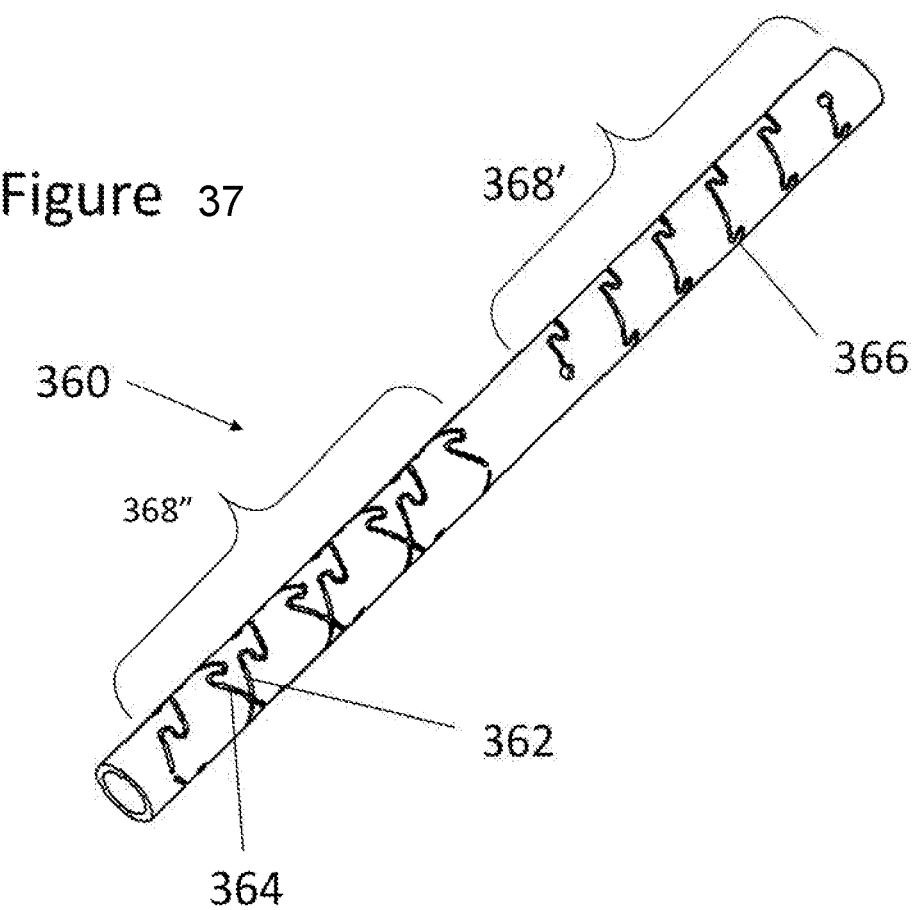

FLEXIBLE SPINE COMPONENTS HAVING MULTIPLE SLOTS

BACKGROUND OF THE INVENTION

Field of the Invention

This invention relates to spinal implants to improved flexible elements for the incorporation in spinal implants. Specifically the invention relates generally to flexible rod connectors for dynamically stabilizing a portion of the spine stabilizing two or more bone segments.

Brief Description of the Prior Art

The use of fixation devices for the treatment of vertebrae deformities and injuries is well known in the art. Various fixation devices are used in medical treatment to correct curvatures and deformities, treat trauma, and remedy various abnormal spinal conditions. Spinal fusion is the standard method of treatment for conditions including spondylolysis, spinal stenosis, and other disc disorders. Since fusions have been expanded to treat more conditions and the number of procedures is rising each year, it is apparent that many surgeons believe the procedure is the best possible treatment for their patients. Over the past decades, a variety of spinal implant devices have been used in conjunction with fusion. These include rigid systems such as bone plates, intravertebral cages, rods and hooks, and pedicle screws. Research shows that, when used properly, pedicle screws are the most reliable spinal implant, providing stabilization even in the event of pseudoarthrodesis. This posterior stabilization system involves variable-angle screws inserted into the pedicle of the vertebrae. Fluoroscopic pedicle screws can be detected by radiographic and fluoroscopic imaging during placement, improving the success rate of surgery. These rigid implants can be inserted from an anterior or a posterior approach, although the majority uses the posterior technique. U.S. Pat. No. 6,645,207 to Dixon teaches a posterior system comprised of bone plates, clamps, and pedicle screws that allow axial stress in order to improve the fusion procedure by placing it under pressure. Compression at the graft interface is crucial to establishing blood supply and nutrients to the graft. The '207 patent demonstrates that physiological loads and stresses are important to achieve proper healing or adjustment of a damaged vertebrae. Similar patents in this field include U.S. Pat. No. 5,437,669 to Yuan, U.S. Pat. No. 5,474,555 to Puno, and U.S. Pat. No. 6,468,276 to McKay.

There are severe limitations of the fusion procedure including unnatural stresses on the vertebrae adjacent to the fusion, extreme limitation of flexional and torsional movements, and frequent in vivo failure of rigid constructs. Problems with spinal fusions stimulated research of dynamic stabilization devices. Dynamic stabilization is an alternative to vertebral body fusion that stabilizes the damaged spine while permitting motion. The instruments used in dynamic fixation emanate from devices used in conjunction with fusion and are embodied in many different inventions. Pedicle screws are used with the majority of these "soft" stabilization methods, and provide physiologic support and controlled motion by attaching to elastic ligaments or metal rods. Soft stabilization devices are designed to restore the biomechanics of a functional spinal segment. Although the soft stabilizing devices relieve many problems caused by fusion, they also increase the chance of implant failure or improper insertion.

Allowing certain degrees of physiologic motion while maintaining proper rigidity to enhance healing is the most difficult aspect of the design process in the field of dynamic spinal stabilization. The Graf ligament is one of the earliest non-fusion techniques, consisting of elastic bands looped around pedicle screws. U.S. Pat. No. 5,092,866 to Breard and Graf describes this system of non-metallic loops, secured to either the spinous processes or pedicle screws, which permit the patient certain degrees of flexional and torsional movements. The semi-elastic ligament keeps sufficient space between the vertebrae which encourages proper healing. This idea has been sophisticated by subsequent researchers who have produced new methods to neutralize unstable vertebrae, and the following are some typical inventions in this field. U.S. Pat. No. 6,966,910 to Ritland describes two pedicle screws anchoring a metallic rod component with several embodiments, including multiple geometries and dual rods. In the '910 device, the geometry of the metal rods produce the flexible or semi-elastic stabilization. U.S. Pat. No. 5,282,863 to Burton teaches a system that achieves dynamic fixation of the spinal column by using a non-metallic, porous material as the rod component, rather than conventional metallic rods, to increase flexibility of the implant. U.S. Pat. No. 7,083,621 to Shaolian utilizes ball-and-socket connections between rods and bone screws that dynamically stabilize the damaged spine. The specialized rods described in the '621 patent can be inserted into the portals of the bone anchors and allow for angular articulation of the device. U.S. Pat. No. 7,018,379 to Drewry teaches a system of bone screws and fasteners that attach a flexible elongated member which is tensioned to provide corrective forces to the spine. Another motion-preserving device presented in U.S. Pat. No. 6,989,011 to Paul incorporates at least one tube with helical slits down the length. This dynamic rod or rods act to support a vertebral motion segment and allow controlled degrees of movement. The angular range of the '011 rod can be modified by altering the pitch and direction of the slits. U.S. Pat. No. 6,293,949 to Justis uses a longitudinal member at least partially composed of a pseudo-elastic shape-memory material that is anchored by bone screws. The longitudinal member reforms to a new configuration under stress then returns to the initial configuration when the stress is removed, providing flexible support for the cervical spine.

Problems with spinal fusions stimulated research of dynamic stabilization devices. Pedicle screws are used with the majority of these "soft" stabilization methods, and provide physiologic support and controlled motion by attaching to elastic ligaments or metal rods. Dynamic stabilization devices are designed to restore the biomechanics of a functional spinal segment. Although the dynamic stabilizing devices relieve many problems caused by fusion, they also increase the chance of device failure or improper insertion.

Subsequent researchers who have produced new methods to neutralize unstable vertebrae have sophisticated this idea introduced by Graf. A flexible posterior stabilization system, DYNESYS (dynamic neutralization system) developed in 1994 and now marketed by Zimmer (Warsaw, Ind.), is now gaining popularity among orthopedic surgeons in the US as an alternative to fusion. Anchored by pedicle screws, Dynesys uses preloaded stabilizing cords and spacers to provide uniform system rigidity. Fusion is an outdated and inelegant technique that permanently eliminates normal biomechanical motion of the spine. The dynamic stabilization systems are important alternatives to fusion and are the future for the treatment of vertebral instability.

A need has thus arisen for improvements in dynamic stabilization instruments, and the present invention offers that advancement through the development of the flexible connecting rod for posterior implantation on damaged vertebrae.

Accordingly it is an object of this invention to provide a flexible components that will flex, bend, or curve to allow or duplicate the natural movement of the spinal segments.

These and other objects, features, advantages and aspects of the present invention will be better understood with reference to the following detailed description of the preferred embodiments when read in conjunction with the appended drawing figures.

SUMMARY OF THE INVENTION

The present invention overcomes the deficiencies and problems evident in the prior art as described herein above by combining the following features into an integral longitudinally, laterally, and torsionally flexible component.

In one embodiment slots of substantial length and width extend in a generally helical path, either continuously or intermittently, around and along a tubular member, following predetermined serpentine, helical paths forming flexible segments. Advantageously, the slots are cut at an angle normal to the shaft using a computer-controlled cutting technique such as laser cutting, water jet cutting, milling, or other means. Additionally, this slot can be cut at an angle to the normal so as to provide an undercut slot; preferably in the range from about 10 to about 45 degrees from the normal. The helical angles can differ within the slot or between slots, either within the same segment or within different segments. The slots have a width of between 2.5% and 10% of the diameter of said spinal element, an angle from about 5 degrees to about 20 degrees, a ratio of amplitude to pitch in the range of from greater than 0.1 to about 0.8 and about 4-6 cycles per diameter length.

The flexible segments can be contiguous or separated by non-slotted sections, depending upon the application. Each slot has a start point, having a starting hole, and an end point, having an ending hole. In one configuration a slot is cut into a first segment in a first rotation direction and a second slot is cut in another segment in a same or different rotational direction. Each of the slots extend from respective start holes to end holes.

In another configuration a second slot is cut into the one or more segments and ascends in a second rotational direction. The start points and end points are spaced from one another and the slots cross sinuous paths. Alternatively, one or more of the flexible segments can have a second slot cut that ascends in the same rotation direction, placing the slots parallel to one another. The start points and end points of the slots in contiguous segments can be the same with the slot pattern changing between segments.

Each of the segments can have a sinuous slot configuration from the group comprising single sinuous slot first rotational direction, single sinuous slot second rotational direction, multiple sinuous slots first rotational direction, and multiple sinuous slots in a first rotational direction and a second rotational direction.

A plurality of slots and slot patterns in one or more flexible segments are employed thereby increasing and controlling the flexibility of the component, relative to a shaft having a single slot of identical pattern. The serpentine path forms a plurality of teeth and complimentary recesses on opposite sides of the slots. The slots have sufficient width to form an unbound joint permitting limited movement in any direction between the teeth and the recesses, thereby providing limited flexibility in all directions upon application of tensile, compressive, and/or torsion forces to the component. In a similar manner the slot can have increased width in one direction compared to another direction thus providing increased flexibility in one direction.

The flexible component can further have different degrees of flexibility along its length achieved by having the pitch of the helical slot vary along the length of the shaft. The varied flexibility corresponds to the variation in the pitch of the helical slot. The helical path can have a helix angle in the range of about 10 degrees to about 45 degrees, and the helix angle can be varied along the length of the shaft to produce correspondingly varied flexibility. Alternatively, the width of the helical slots can vary along the length of the shaft to provide the varied flexibility. The rigidity of the flexible shaft can be achieved through the design of the slot patterns, thereby enabling the use of thinner walls than would otherwise be required to produce equivalent rigidity. In a preferred embodiment, the ratio of the amplitude of the serpentine path to the pitch of the slot is in the range from greater than 0.1 to about 0.8.

The slots can be filled with a resilient material, partially or entirely along the path of the slot. The resilient material can be an elastomer compound which can be of sufficient thickness to fill the slot and to encapsulate the entire shaft thus forming an elastomer enclosed member. The elastomer can be a resilient material such as a urethane or a silicone compound. The rigidity of the flexible shaft can be further achieved or varied through the use of filler material having different stiffness properties, thereby enabling the use of thinner walls than would otherwise be require to produce equivalent rigidity.

Preferably, the flexible shaft is formed by laser cutting an elongated tubular member of substantial wall thickness, to form the slot around and along the tubular member in a helical manner. A serpentine path can be superimposed on a helical wave in the form of a generally sinusoidal wave.

Preferably, the sinusoidal wave forms dovetail-like teeth, which have a narrow base region and an anterior region which is wider than the base region. Thus, adjacent teeth interlock. The teeth can have a configuration as illustrated in U.S. Pat. No. 4,328,839, the disclosure of which is incorporated herein by reference, as though recited in detail.

BRIEF DESCRIPTION OF THE DRAWINGS

These and other objects, features, advantages and aspects of the present invention will be better understood with reference to the following detailed description of the preferred embodiments when read in conjunction with the appended drawing figures.

FIG. 11 a horizontal view of the flexible spinal element 70 of FIG. 10 showing the location of Sections A-A and B-B;

FIG. 12 is a longitudinal, cross sectional view of the flexible spinal element of FIGS. 10 and 11 through the cross section A-A in longitudinal axis of FIG. 11, showing general pattern of the serpentine slots along the length of the element and showing the elastomer material within the slot in accordance with the invention;

FIG. 13 is a view of section B-B in FIG. 11 showing the elastomer material within the slot in accordance with the invention;

FIG. 14 is an illustration of the flexible spinal element 80 segment with an elastomeric coating covering the flexible region of element 80;

FIG. 15 is the sectional view of Section A-A in FIG. 14;

FIG. 16 is a the sectional view of Section B-B in FIG. 14 showing the elastomer coating the interior and exterior surface of the shaft and within the slot;

FIG. 17 is an illustration the flexible spinal element 90 segment with a resilient filler covering the flexible region, filling the slot and filling the interior cavity in accordance with the invention;

FIG. 18 is a sectional view of the Section A-A showing complete filling of the slot and interior cavity of the flexible spinal element 90 segment in FIG. 17 in accordance with the invention;

FIG. 19 is a cross sectional view of the Section B-B of FIG. 17 showing complete filling of the slot and interior cavity of the flexible spinal element 90 segment in accordance with the invention;

FIG. 22 is the horizontal view of the double helix pattern flexible shaft in FIG. 20;

FIG. 23 is a magnified view of the area B of FIG. 21 in accordance with the invention;

FIG. 24 is a magnified view of the area C of FIG. 21 in accordance with the invention;

FIG. 37 illustrates a shaft having a double slot, each slot ascending in an opposite direction, and a single slot in a second segment, in accordance with the invention; and, FIGS. 38A-38F illustrate alternate slot patterns in accordance with the invention.

DESCRIPTION OF THE PREFERRED EMBODIMENT

Definitions

Figure 1A:
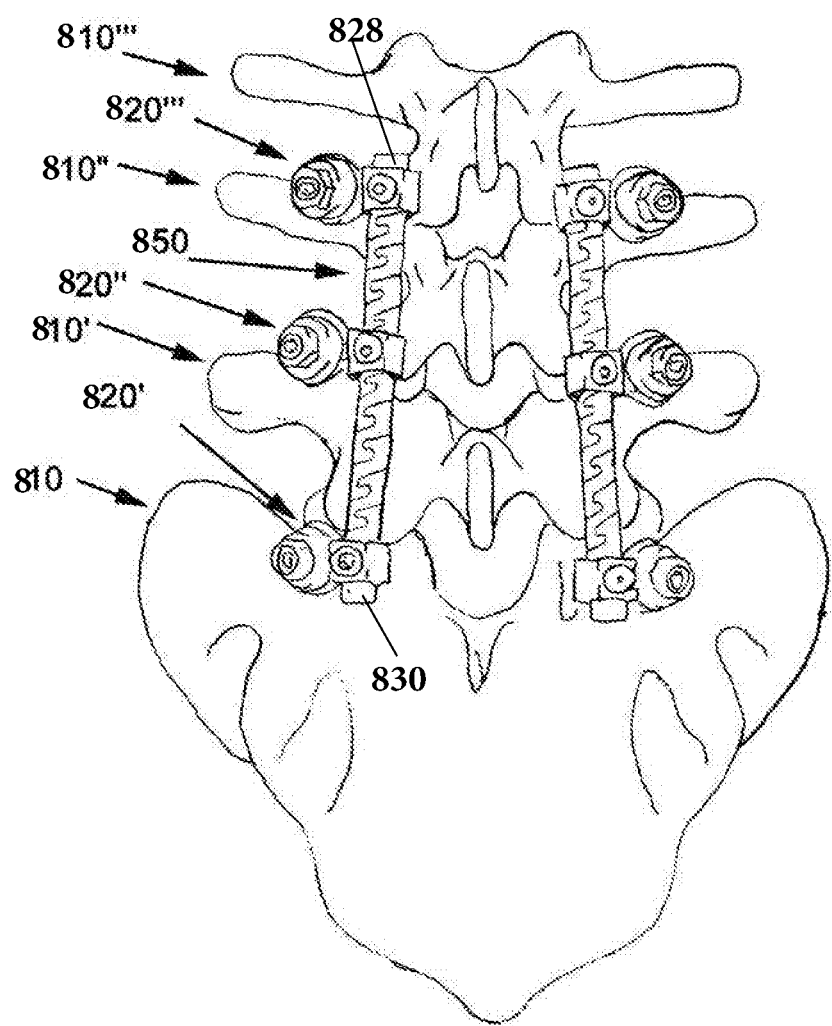
FIG. 1A is a schematic representation of a flexible spinal element attached to the lumbar region of the spine and having the helical slot extending the majority of the length of the element in accordance with the invention.

For the purposes herein the terms "slit" and "slot" are used interchangeably, consistent with their definitions, as follows:

Slot—n.
 a. A narrow opening; a groove or slit: a slot for coins in a vending machine; a mail slot.
 b. A gap between a main and an auxiliary airfoil to provide space for airflow and facilitate the smooth passage of air over the wing.

For the purposes herein the term "pitch" as used herein is defined as:

Pitch—n.
 a. The distance traveled by a machine screw in one revolution.
 b. The distance between two corresponding points on adjacent screw threads or gear teeth. (American Heritage Dictionary, 3rd Edition, Copyright 1994)

For the purposes herein the term "cycle" as used herein is defined as:

Cycle—
a. An interval of time during which a characteristic, often regularly repeated event or sequence of events occurs: Sunspots increase and decrease in intensity in an 11-year cycle.
b. A single complete execution of a periodically repeated phenomenon: A year constitutes a cycle of the seasons.
c. A periodically repeated sequence of events: cycle includes two halves of the sine-wave like undulation of the slot path. (American Heritage Dictionary, 3rd Edition, Copyright 1994)

For the purposes herein the term "amplitude" shall refer to the maximum absolute value of the periodically varying quantity of the slot.

For the purposes herein the term "serpentine" shall refer to:
a. winding or turning one way and another <a serpentine road>.
b. having a compound curve whose central curve is convex. (Merriam-Webster online dictionary)

For the purposes herein the term "sinuous" shall refer to:
a. of a serpentine or wavy form: winding,
b. marked by strong lithe movements. (Merriam-Webster online dictionary)

The terms sinuous and serpentine are used interchangeably herein.

For the purposes herein the term "helical", "helix" and "spiral" are used interchangeable and shall refer to:
a1. winding around a center or pole and gradually receding from or approaching it <the spiral curve of a watch spring>
a2. helical
a3. spiral-bound <a spiral bound notebook>.
b. of or relating to the advancement to higher levels through a series of cyclical movements. (Merriam-Webster online dictionary)

For the purposes herein the term "about" shall refer to plus or minus ten percent (10%).

For the purposes herein the term "approximate" shall refer to plus or minus ten percent (10%).

For the purposes herein the term "helix angle" or "helical angle" shall refer to the angle, $\phi$, between the overall helical path of the slot and the axis normal to the longitudinal axis of the shaft, as illustrated in FIG. 2. The helix angle, $\phi$ can be found by unraveling the helix slot from the shaft, FIG. 2, representing the section as a right triangle, and calculating the angle that is formed.

Helix angle, $\phi 212 = \arctan(P/\pi D)$ where;
a. P is the pitch, lead or rise of the slot 214
b. D is the diameter of the shaft 216

For the purposes herein the term "slot angle" shall refer to the angle of the slot relative to a plane tangent to the longitudinal axis of the shaft.

For the purposes herein the term "frequency" shall refer to the number of times a specified phenomenon occurs within a specified interval:
Frequency.
a. Number of repetitions of a complete sequence of values of a periodic function per unit variation of an independent variable.
b. Number of complete cycles of a periodic process occurring per unit time.
c. Number of repetitions per unit time of a complete waveform, as of an electric current. The number of times the cycles form a repetitive pattern in one unit of length is the frequency of the slot pattern. The number of cycles of the slot undulations superimposed upon the circumferential path which are present in one revolution around the shaft is referred to as the cycles per revolution. (American Heritage Dictionary, 3rd Edition, Copyright 1994).

As used herein the term "shaft" and "element" shall be used interchangeably and refer to the hollow rod or tube used to provide spinal support.

The term slot as used herein, is defined in the American Heritage Dictionary, 3rd Edition, Copyright 1994, as follows:
For the purposes herein the term "spiral" shall refer to:
Spiral
a1. A curve on a plane that winds around a fixed center point at a continuously increasing or decreasing distance from the point.
a2. A three-dimensional curve that turns around an axis at a constant or continuously varying distance while moving parallel to the axis; a helix.
a3. Something having the form of such a curve: a spiral of black smoke.
b. Printing. A spiral binding.
c. Course or flight path of an object rotating on its longitudinal axis.
d. A continuously accelerating increase or decrease: the wage-price spiral.
Spiral (adj.)
a. Of or resembling a spiral.
b. Circling around a center at a continuously increasing or decreasing distance.
c. Coiling around an axis in a constantly changing series of planes; helical.
d The spiral is more explicitly helix-like, in that it is a three-dimensional curve that lies on a cylinder, so that its angle to a plane perpendicular to the axis is constant. However, along the length of the shaft, or element, the helix angle can vary so as to impart changes in flexibility to the overall shaft. Using an electronics analogy, the helix can be viewed as a carrier wave with the slot following the path of the modulation of the carrier wave. The teeth or interlocking regions of the cycle, form a ratchet-like structure, in that one set of teeth engage the other set of sloping teeth, permitting motion in one direction only.

For the purposes herein the coined term "Biofidelic" shall refer to the mechanical structures that attempt to duplicate biological structures with a high accuracy of fidelity.

For the purposes herein the term "spinal element" shall refer to a hollow rod or tube manufactured of a biocompatible material that can receive a slot or cut to provide flexibility.

For the purposes herein the term "flexible segment" shall refer to the individual flexible sections of a flexible spinal element.

For the purposes herein the term "segment unit" shall refer to the flexible segments and adjacent end attachment segment divided by one or more center attachment segments.

DETAILED DESCRIPTION OF THE PREFERRED EMBODIMENTS

While the present invention will be described more fully hereinafter with reference to the accompanying drawings, in which particular embodiments and methods of implantation are shown, it is to be understood at the outset that persons skilled in the art can modify the invention herein described, within the criteria set forth, while achieving the functions and results of this invention. Accordingly, the descriptions that follow are to be understood as illustrative and exemplary of specific structures, aspects, and features within the broad scope of the present invention and not as limiting of such broad scope.

The present invention is directed to dynamic stabilization systems for use with the anterior, antero-lateral, lateral, and/or posterior portions of at least one motion segment unit of the spine. The systems of the invention are designed to be conformable to the spinal anatomy and provide controlled, dynamic stabilization.

The system of the invention can be used on the cervical, thoracic, lumbar, and sacral segments of the spine. For example, the size and mass increase of the vertebrae in the spine from the cervical to the lumbar portions is directly related to an increased capacity for supporting larger loads. This increase in load bearing capacity, however, is paralleled by a decrease in flexibility and an increase in susceptibility to strain. When rigid immobilization systems are used in the lumbar segment, the flexibility is decreased even further beyond the natural motion restriction of that segment. Replacing the conventional rigid immobilization systems with the disclosed spine stabilization system restores a more natural movement and provides added support to the strain-susceptible area.

The spine stabilization system of the present invention includes bone fasteners, for example pedicle screws, the disclosed end plates or hooks, and at least one flexible spinal element with or without additional connecting rods. The flexible element advantageously provides desirable properties for bending or twisting that allows the system to accommodate the natural spine movement. The flexible element preferably approximates or resembles a relatively circular metallic or polymeric tube or rod with an appropriately formed slot that extends spirally around the flexible spinal element either continuously or segmentally, the basic concept of which is described by Krause et al (U.S. Pat. Nos. 6,053,922 and 6,447,518). In another embodiment, the spinal element and flexible segments of the element can be combined with a polymeric material as described hereinafter.

In some embodiments the central portion of the flexible element is hollow, resembling a hollow tube. A skilled artisan would appreciate that there are several ways to form a hollow tube, regardless of whether it is circular or any other cross-sectional shape. For example, extruding a material, such as metal or polymeric materials, through a die, can form the tube. One or more of the patterns described hereinafter can then be cut into the extruded material. For instance, a tube can have a helical spiral slit or serpentine cut along at least a portion of the tube or the tube can have a plurality of diagonal slits cut into its surface, by using a laser or by other suitable methods.

The following examples describe embodiments using a hollow rod or tube. It should be understood that in these examples the flexible elements described herein can be replaced with flexible elements having different shapes or configurations, including, but not limited to, the many variations described herein.

The disclosed system has several closely related embodiments, all using the flexible spinal element. The selection of a specific embodiment for a particular application will be obvious to one skilled in the medical arts upon reading the teachings herein.

The invention relates to a flexible spine stabilization system having one or more flexible segments within a spinal element. The flexibility is created through the use of at least one helical slit formed in the spinal element. Additional flexible segments also have at least one helical slit in either the same helical rotation or pattern or in an opposite rotation and/or different pattern. One or more fasteners are connected to or in communication with the distal and proximal attached ends of the spinal elements as known in the medical arts. In another embodiment the flexible spine stabilization system has a flexible segment that has at least one helical, serpentine slot within a section of the spinal element that is embedded within a polymer or other flexible material so as to fill the slot with the flexible material. In an additional embodiment the flexible spine stabilization system uses a hollow flexible element that encompasses a polymer or other flexible material within its central core without extending into the helical slot(s). A further embodiment uses a flexible slotted segment within the spinal element that contains a polymer or other flexible material within the central core with the flexible material extending radially outward through the helical, serpentine slot(s). The flexible spine stabilization system can further incorporate a flexible slotted segment that contains a polymer or other flexible material within the central core of the spinal element and/or flexible segment that extends radially outward through the slot and encompasses the outer surface of the spinal element and/or the flexible segment.

The dynamic stabilization system of the present invention generally consists of a spinal element 850 and pedicle screws 820, as illustrated in FIG. 1A, which are connected to two or more vertebra 810, 810', 810" and 810''' spanning the area fused or damaged area. The spinal element 850 in this embodiment generally consists of a hollow tube having an outer surface and a hollow central core as illustrated hereinafter. Slots are cut through the wall of the spinal element 850 to form serpentine, helical paths that extend generally along spiral paths around the entire length of the spinal element 850. The extension of the helical slot or slots continually over most of the length of the spinal element 850 enables the majority of the element 850 to flex. Although pedicle screws 820 are illustrated herein as being attached to the proximal attachment end 828 distal attachment end 830, as well as the central portion of the spinal element 850, hooks or other known attachment members can be substituted as known in the art. It should be noted that the pedicle screws can be affixed to slotted portions of the spinal element as well as non-slotted portions as illustrated in FIG. 1B.

Figure 1B:
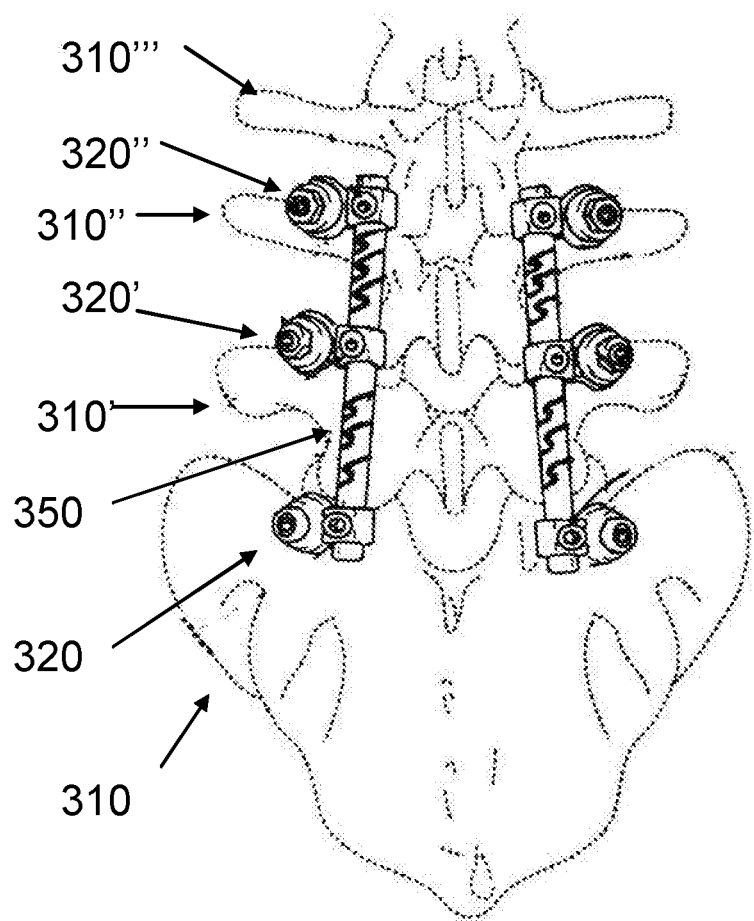
FIG. 1B is a schematic representation of an alternate flexible spinal element; showing general pattern of the helical serpentine slot along portions of the length of the rod in accordance with the invention.

In FIG. 1B the dynamic stabilization system of the present invention generally consists of a spinal element 350 and pedicle screws 320 which are connected to two or more vertebra 310, 310', 310" and 310''' spanning the fused or damaged area. As with the embodiment of FIG. 1A, the spinal element 350 of FIG. 1B generally consists of a hollow tube having an outer surface and a hollow central core as illustrated in hereinafter in the disclosed embodiments. As illustrated in subsequent figures, slots are cut through the wall of spinal element segments to form flexible segments having a serpentine, helical path.

Although FIGS. 1A and 1B illustrate two flexible sections, the number would be dictated by the number of vertebral discs requiring flexible support and would be obvious to those skilled in the art. Additionally, only a single slot per segment is illustrated in FIGS. 1A and 1B, any of the multiple slots per segment as illustrated herein would be applicable.

Figure 2A:
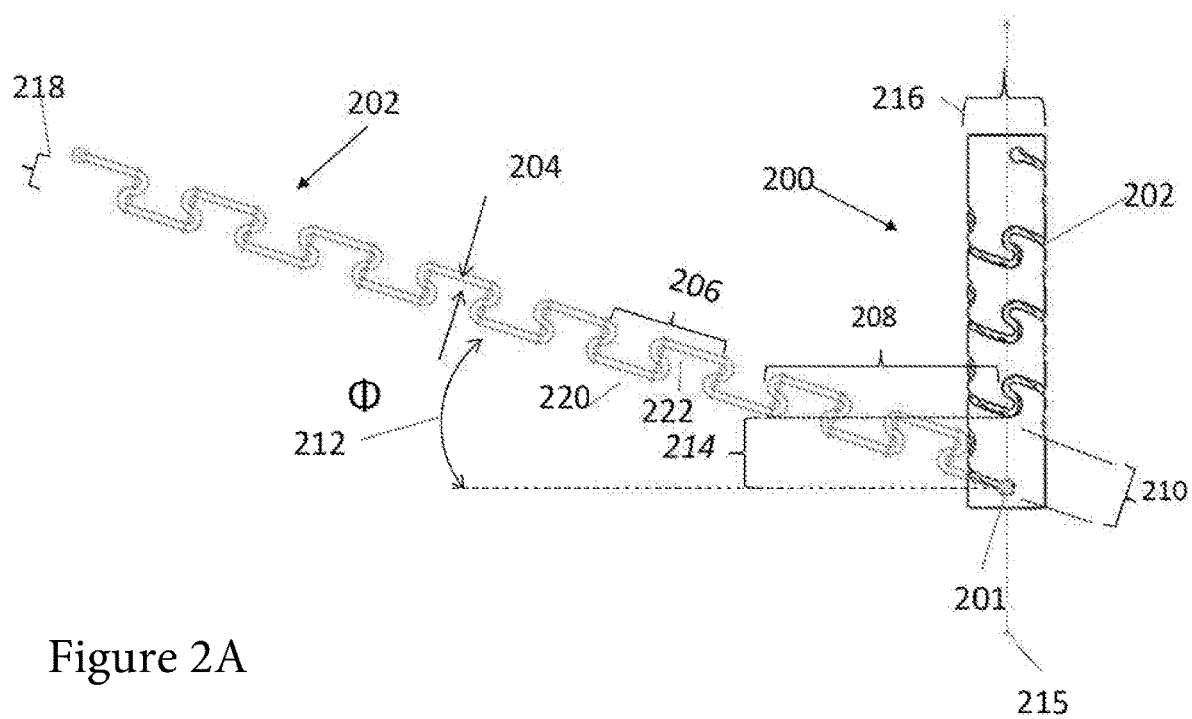
FIG. 2A illustrates the nomenclature used for the description of the sinuous helical slot, in an unwrapped condition of a flexible spinal element segment.
Figure 2B:
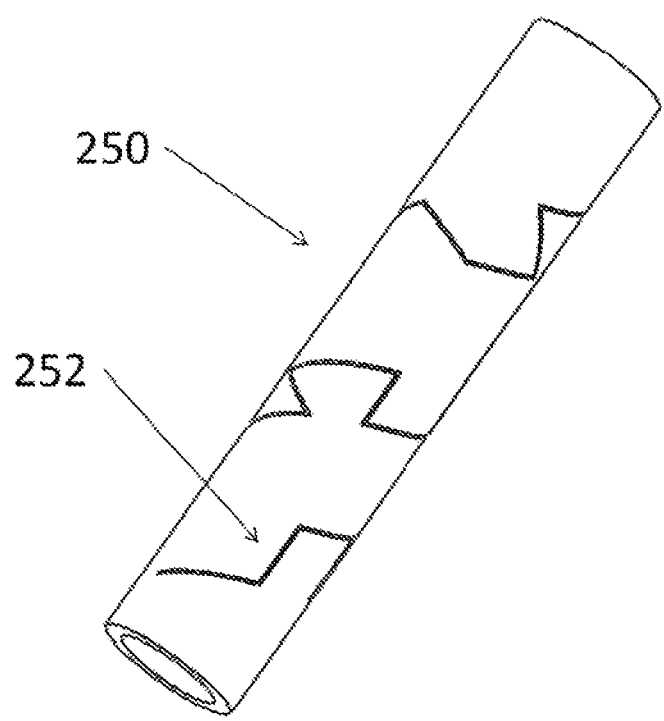
FIG. 2B illustrates a helical slot 252 on the flexible spinal element 250 having a straight configuration or combination of straight and curved portions that are in a random or repetitive pattern.

To better illustrate and define one of the characteristics of the invention, FIG. 2A illustrates a representative section of a flexible spinal element 200 containing a slot 202 following a sinuous path about a helical path along the longitudinal surface of the spinal element. For Illustrative purposes, the sinuous path of the slot 202 is "unwrapped" from the spinal element 200 to show the properties of the slot 202 and corresponding relationships.

Figure 2C:
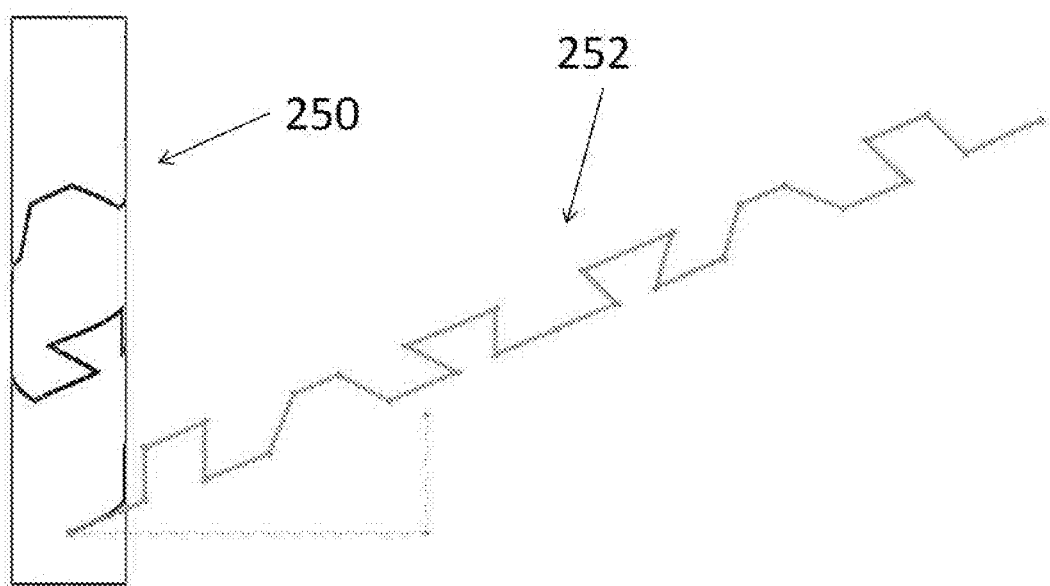
FIG. 2C illustrates the sinuous path of the slot 252 "unwrapped" from the flexible spinal element 250 to show the non-uniformity and repetitiveness of the slot configuration.

As illustrated, the spinal element 200 has a diameter 216 and a longitudinal axis 215. The slot 202 is formed from a number of cycles 206, each having a proximal dovetail tooth 220 and a distal dovetail tooth 222. The length of the cycles 206 contribute to the degree of flexibility and can vary over the length of the slot 202. The number of cycles 206 will also be determined by the circumference 208 of the flexible spinal element 200 into which is cut helical slot 202. The helix rise 210, or distance between proximal end 201 and subsequent cycles 206 of the slot 202, is determined based on desired flexibility. Other contributing factors to the degree of flexibility are the amplitude 218, or the height of the proximal tooth 220 and distal tooth 222 and the slot width 204. The helix angle 212 and the pitch 214 are further contributors to flexibility. Although the cycles ascending the slot are aligned in this and other figures, alignment is not a critical feature and the cycles can, and will with pattern changes, be unaligned In another embodiment of the invention illustrated in FIG. 2B a helical slot 252 on the spinal element 250 has a straight configuration or combination of straight and curved portions that are in a random or repetitive pattern. FIG. 2C illustrates the sinuous path of the slot 252 "unwrapped" from the spinal element 250 to show the non-uniformity and non-repetitiveness of the slot configuration.

It should be noted that when a flexible spinal element has more than one flexible segment, or more than one slot per segment, the slot width, helix angle, pitch, cycle length and amplitude can all vary from slot to slot, segment to segment or within a single slot. This is applicable for all embodiment herein.

Figure 3:
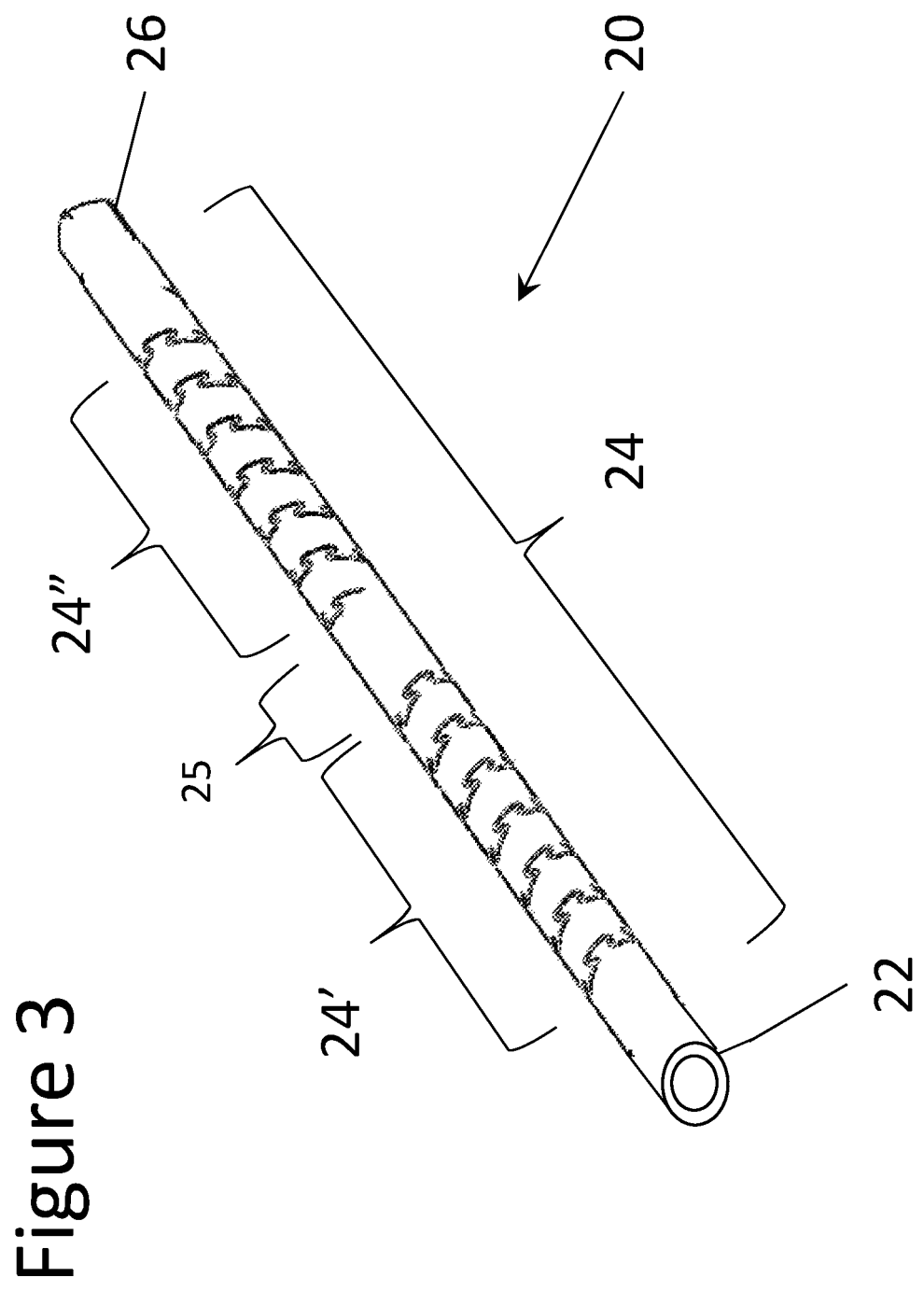
FIG. 3 shows a flexible spinal element 20 unit in accordance with the invention composed of one or more flexible segments 24' and 24" forming the flexible portion 24 of the element 20.

FIG. 3 shows a flexible spinal element 20 unit in accordance with the invention composed of one or more flexible segments 24' and 24" forming the flexible portion 24 of the element 20. The flexible segment 24' in this embodiment ascends toward the attachment section 22 while the flexible segment 24" ascends toward the attachment section 26. As the illustrated flexible spinal element 20 spans two vertebra, a middle securing segment 25 is required. In this illustration the securing segments 22, 25, and 26 are un-slotted and used for placement of the securing member. As known in the art, the longer the flexible spinal element in any embodiment, the more securing portions will be required.

The different directions of ascension provide a net zero longitudinal displacement of the flexible portion 24 when the flexible portion 24 is subjected to torsional forces.

Figure 4:
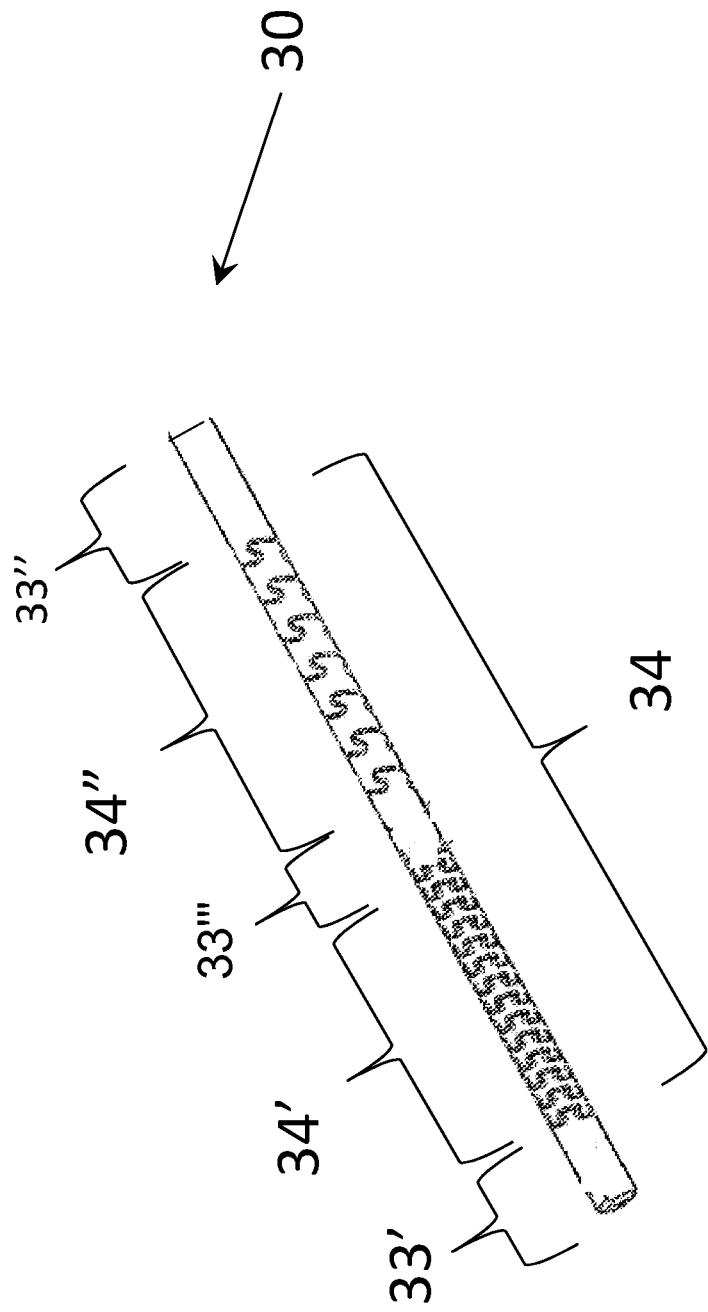
FIG. 4 shows a flexible spinal element 30 unit in accordance with the invention having a central flexible shaft 34 composed of one or more flexible segments 34' and 34"

FIG. 4 shows a flexible spinal element 30 unit in accordance with the invention illustrating the securing segments 33', 33" and 33''', and a central flexible spinal element 34 composed of two flexible segments, clockwise distal segment 34' and counterclockwise proximal segment 34".

Figure 5:
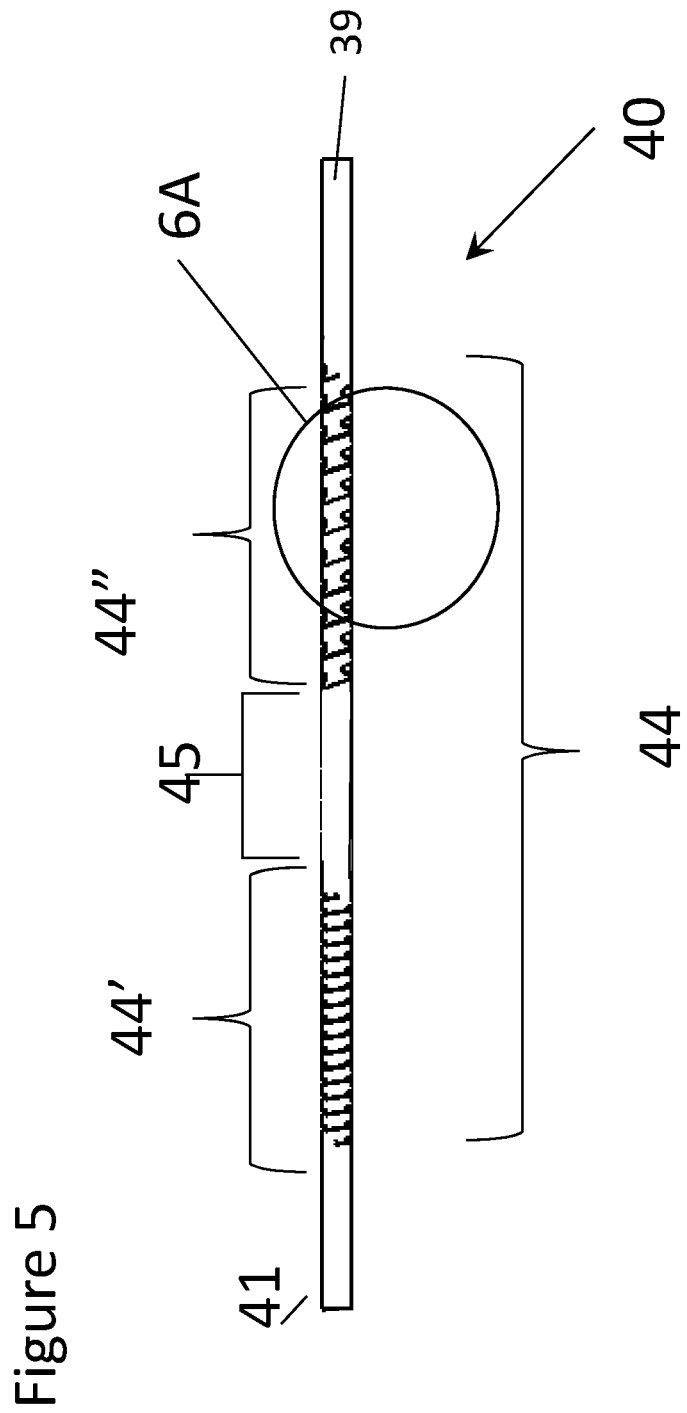
FIG. 5 shows an example of a flexible spinal element 40 configuration that can be used with any of the disclosed embodiments.
Figure 6:
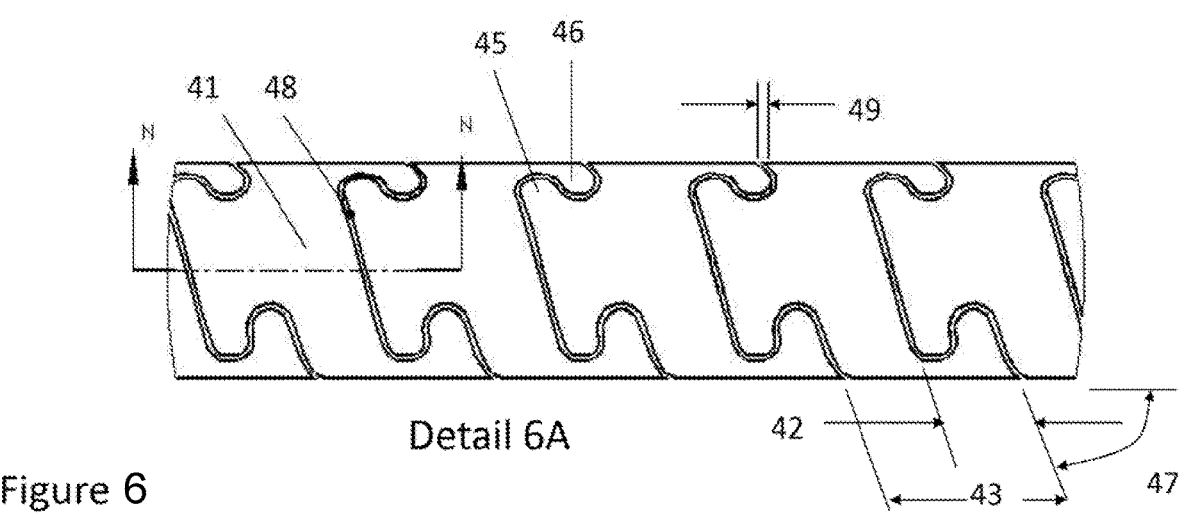
FIG. 6 is a detailed view of the serpentine slot comprising the flexible segment shown in 6A FIG. 5 in accordance with the invention.

FIG. 5 is a diagrammatic illustration of a generalized flexible spinal element 40 which has a distal securing segment 41, flexible section 44 divided into two flexible segments, distal segment 44' and proximal segment 44" and a proximal securing segment 39. The distal segment 44' and the proximal segment 44" is divided by securing segment 45. The exploded area of FIG. 6 is indicated in FIG. 5 by 6A. In this embodiment flexible section 44' and flexible section 44" have different helical patterns, however this is for example only as is the length of each flexible section.

FIG. 6 is an exploded view of section 6A in FIG. 5 showing the serpentine slot 48 of the flexible section 44" of the flexible spinal element 40. The slot 48, having a slot gap width 49, is cut with a general helix angle 47 of about 10 to 80 degrees with respect to the longitudinal axis of the section 44". The slot 48 is cut in a serpentine pattern having an amplitude 42 and interlocking teeth 46, 45 with a pitch 43. Typically the ratio of the amplitude 42 to the spacing 43 is between 0.1 and 0.8. For a higher angled slot helix, the spacing amplitude can be lower.

Figure 7:
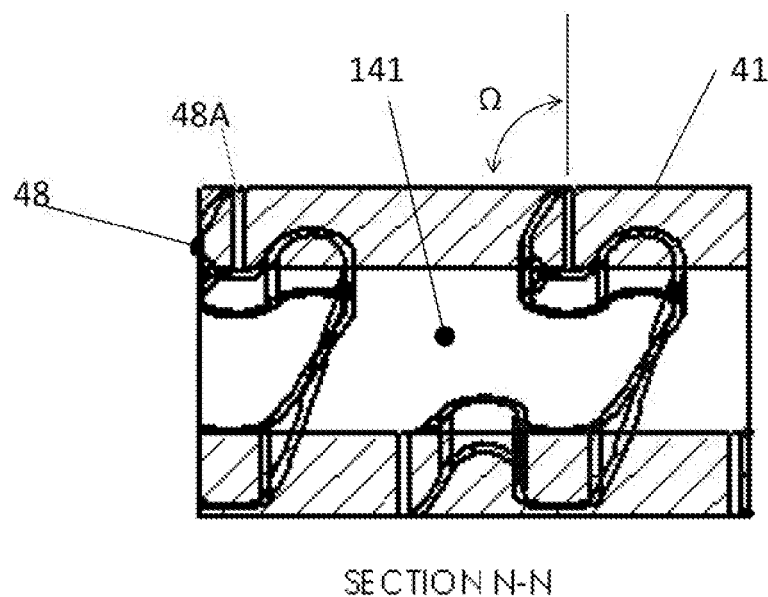
FIG. 7 is a sectional view of section N-N in FIG. 6 in accordance with the invention.
Figure 21:
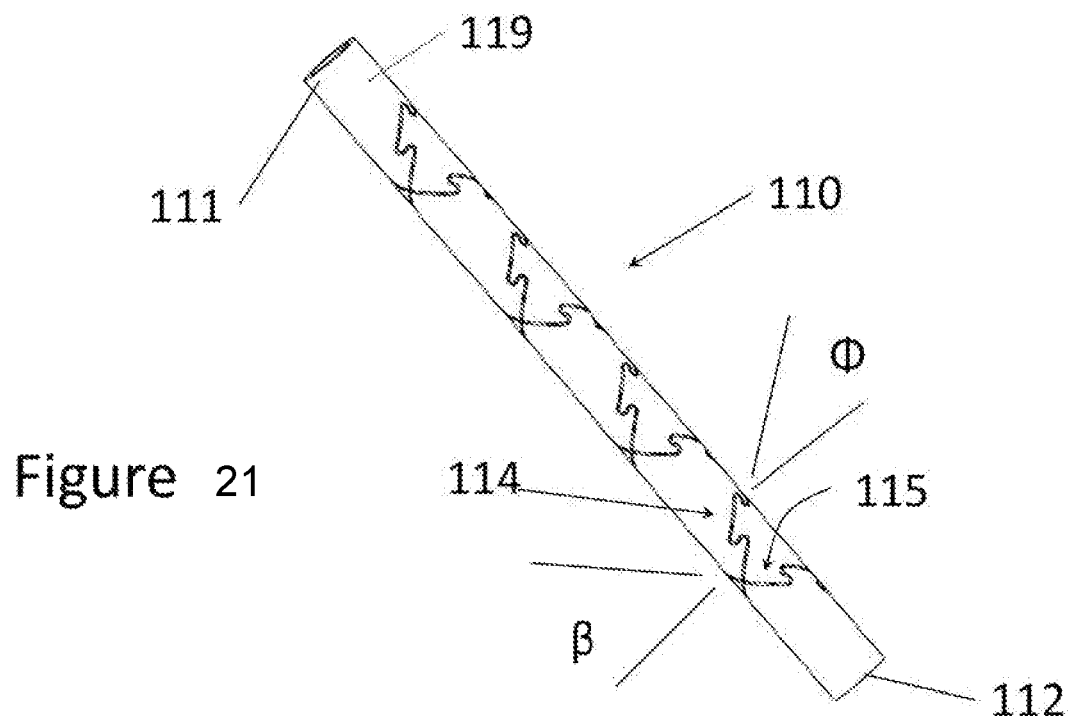
FIG. 21 is an isometric view of FIG. 20.

FIG. 7 illustrates the section view N-N of FIG. 6. The slot 48 is representative of all the slots disclosed herein in the way that it is cut through the spinal element 40 into the interior cavity 141 with the depth 48A of the slot 48 being equal to the thickness of the element 40. Although the slots disclosed herein are of different patterns, this is purely a function of flexibility and all have the same basic construction. In the following descriptions of the criteria of the slots, no reference numbers specific to other figures are used, as the criteria are applicable to all slot configurations. Advantageously, the slot is cut perpendicular to a plane tangent to the outer surface of the flexible spinal element as shown in FIG. 7. Alternatively, the slot can be cut at some slot angle Ω to the longitudinal axis of the element and/or the plane tangent to the outer surface, as shown in FIG. 21. The angle can be in the range from zero (perpendicular) to about 75 degrees thereby forming an undercut. Preferably the angle if not perpendicular, is in the range from about 30 to 45 degrees from the perpendicular. The undercut can be formed by cutting offset from the radius, or offsetting from a plane tangential to the surface of the element at the slot.

Figure 8:
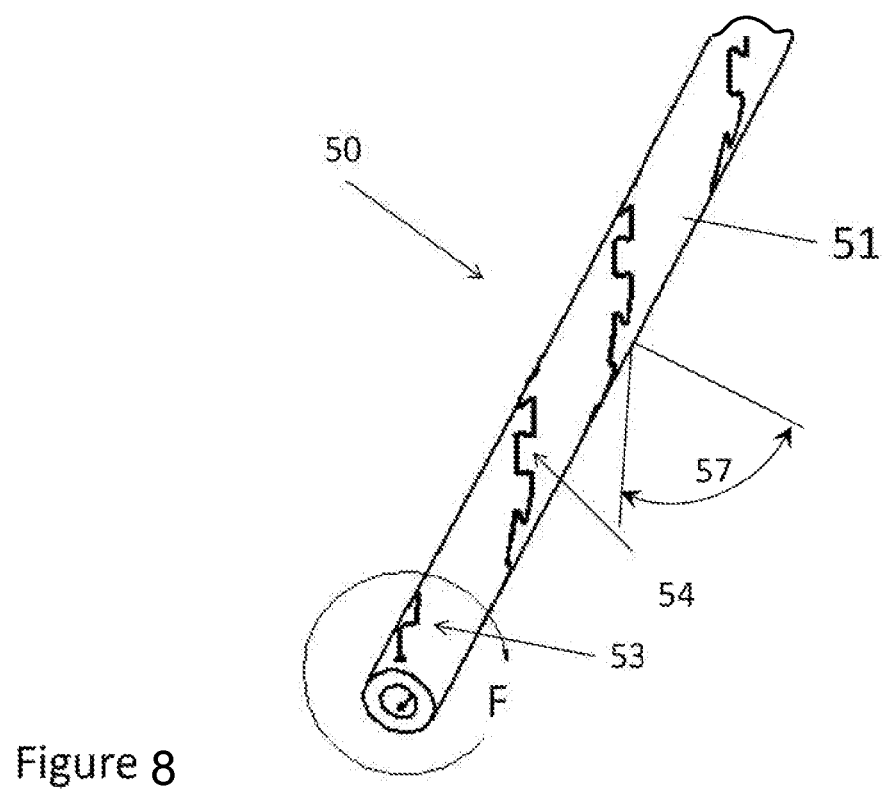
FIG. 8 shows a segment of a flexible spinal element segment 50 with a sinuous helical slot at a high angle relative to the element in accordance with the invention.
Figure 9:
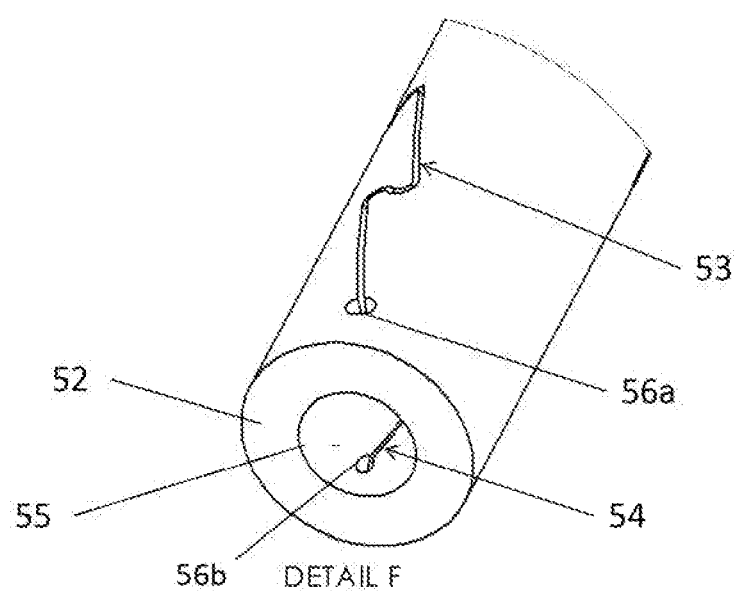
FIG. 9 is a detail view of Detail F in FIG. 8 in accordance with the invention.
Figure 10:
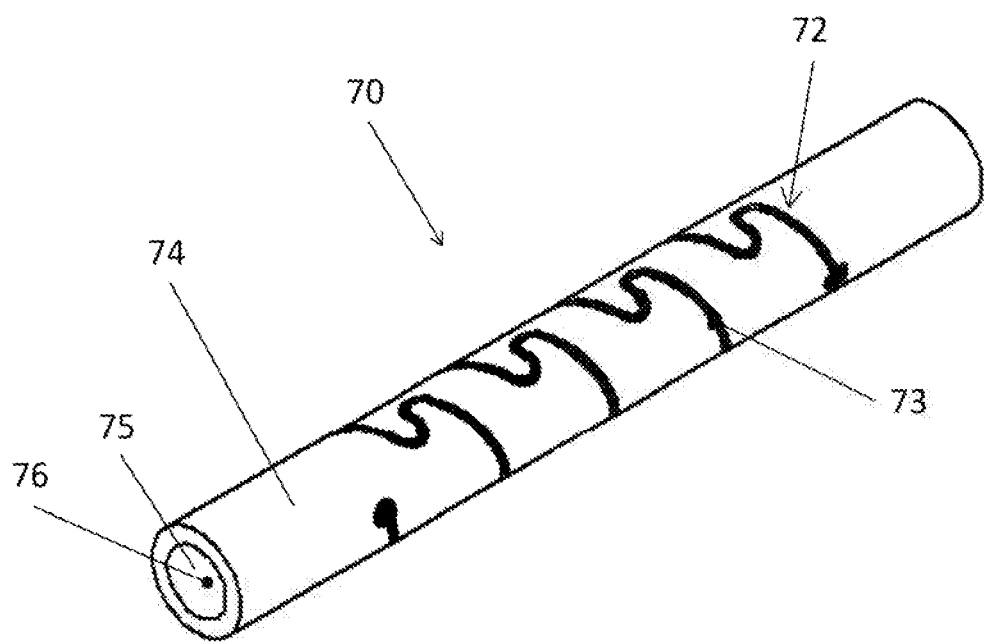
FIG. 10 is a schematic representation of a segment of a flexible spinal element 70 segment, showing a general pattern of the sinuous, serpentine slots along the length of the element with an elastomeric material filling the slot in accordance with the invention.

The flexible spinal element 50, as illustrated in FIGS. 8 and 9, consists of a hollow tube 58 having wall 52 with an outer surface 51 and a hollow central core 55 with two slots 53 and 54. In this instance the slots 53, 54 are cut into the wall 52 at a very high helix angle 57 relative to a line normal to the longitudinal axis of the flexible spinal element 50. In FIGS. 8 and 9 the securing segment has been eliminated in order to more clearly illustrate the ending of the slots 53 and 54. Detail F of FIG. 9 shows the start of the slots 53 and 54 having circular ends 56a and 56b respectively, to reduce the stress concentration at the end of the slot. The use of the circular ends 56a and 56b at the beginning and end of all slots reduces the stress at the end of the slot and substantially reduces the risk of the shaft cracking or breaking under pressure. Although in some uses the pressure applied will not be sufficient to break the shaft, in many industrial uses the pressure applied can cause damage.

It should be noted that in FIGS. 8 and 9, as well as other figures herein, the securing segments have been shortened or eliminated to clearly illustrate additional features.

In order to provide the desired flexibility, while maintaining support, the width of the slot will be dependent upon the desired flexibility, dimensions of the element and the helix angle. Generally, a rod having a diameter in the range from about 0.10 to about 1.5 inches when the helix angle is less than 45 degrees, the slot width should not exceed of about 0.005 to about 0.15 inches. Or alternatively stated, the slot width is between about 2.5% and about 20% of the diameter of the element. The slot width typically determines the flexibility of the element; a larger slot width produces a more flexible element than an element with a smaller slot width. The ratios between slot design and element diameter to achieve optimum flexibility and torque are dependent upon end use. Using the teachings set forth herein, a person skilled in the art can determine the optimal slot design to diameter based on the end application.

In order to prevent tissue growth into the slots that would hinder flexibility, the slots can be filled with a resilient flexible or elastomeric material. The degree of filling can vary from just the slots being filled to the entire central cavity and exterior of the element being filled. Representative variations, although not exhaustive, in the amount of filling is illustrated in the following figures. It should be noted that the type of elastomeric material used can also be varied in its material properties, thereby further controlling the amount of flexibility. In addition to preventing tissue growth into the slots and controlling flexibility, the elastomeric material can provide some structural integrity to the element, permitting wider slots to be used in some applications. The degree of added integrity is dependent upon the application of the elastomeric material as well as the elasticity of the material.

The embodiment illustrated in FIGS. 10 through 13 shows a resilient flexible or elastomeric material 73 filling only within the slot 72 of the flexible spinal element 70. The exterior surface 74 of the flexible spinal element 70, as well as the hollow interior cavity 76, remains uncovered by the elastomeric material 73 as does the interior surface 75. The addition of the elastomeric material 73 to the slot 72 provides resistance to the flexibility of the element 70 as well as preventing tissue growth into the slots. FIG. 11 shows a longitudinal view of flexible spinal element 70 and FIGS. 12 and 13 show the sections A-A and B-B of the flexible spinal element 70, respectively. FIGS. 12 and 13 show the elastomeric material filling 73 only within the slot 72 in both a cutaway side view and an end view.

It should also be noted that the elastomeric material does not necessarily have to fill all slots in the element, with the placement of filled and unfilled slots affecting the flexibility. In most applications, however, unfilled slots would be covered on the exterior of the spinal element with elastomeric material to prevent tissue growth within the slots.

The embodiment illustrated in FIGS. 14, 15 and 16, has a resilient flexible or elastomeric material 83 filling the slot 82 as well as covering both the interior surface 85 and exterior 84 surfaces of the flexible spinal element 80. FIGS. 15 and 16 show the sections A-A and B-B of the flexible spinal element 80 of FIG. 14, respectively. FIG. 15 illustrates the interior surface 85 of the element 80 coated along with the coated exterior 84 and filled slots 82. FIG. 16 illustrates the elastomeric material 83 completely filling the slot 82 and coating the interior and exterior surfaces.

In another variation, only the exterior surface or the interior surface of the element remains uncovered by the material, with the opposing surface being covered. The combinations taught herein are for example only and any combination of elastomeric material covering and/or filling with any design, helical angle, slot angle or number of slots can be used to vary the flexibility.

The embodiment illustrated in FIGS. 17, 18 and 19, shows a resilient flexible or elastomeric material 93 filling the central hollow interior cavity 96 of the flexible spinal element 90 segment, the slot 92 and the exterior surfaces 94. This embodiment provides the greatest resistance to flexing when using the hollow flexible spinal element and elastomeric filling of the central interior cavity 96. Although only the portion of the flexible spinal element 90 having a slot 92 is shown filled with the elastomeric material 93, the unslotted portions of the hollow interior cavity 96 can also be filled.

In another embodiment, the flexible spinal element has multiple serpentine, sinuous slots about the element either in a clockwise and/or counter-clockwise rotation in a helical fashion. Cutting a single helical slot into a tube yields what is referred to as a single-slot element. Similarly, a double-helix spinal element can be constructed provided that the helix angle is the same, and a second slot is cut in the space between the slots of the first. For certain applications, triple and quadruple slots are in use. In another aspect of the invention, one or more sections of the element, have both the serpentine helical slot spiral in one direction and a second section, or multiple sections, rotated in the opposite direction. Another aspect of the invention is to have a double helix with one or more helix rotated in a clockwise direction, and a second or more helixes in a counter-clockwise rotation within the same section of the element. With the combination of clockwise and counter clockwise rotations, the elongation or contraction can be minimized.

Figure 20:
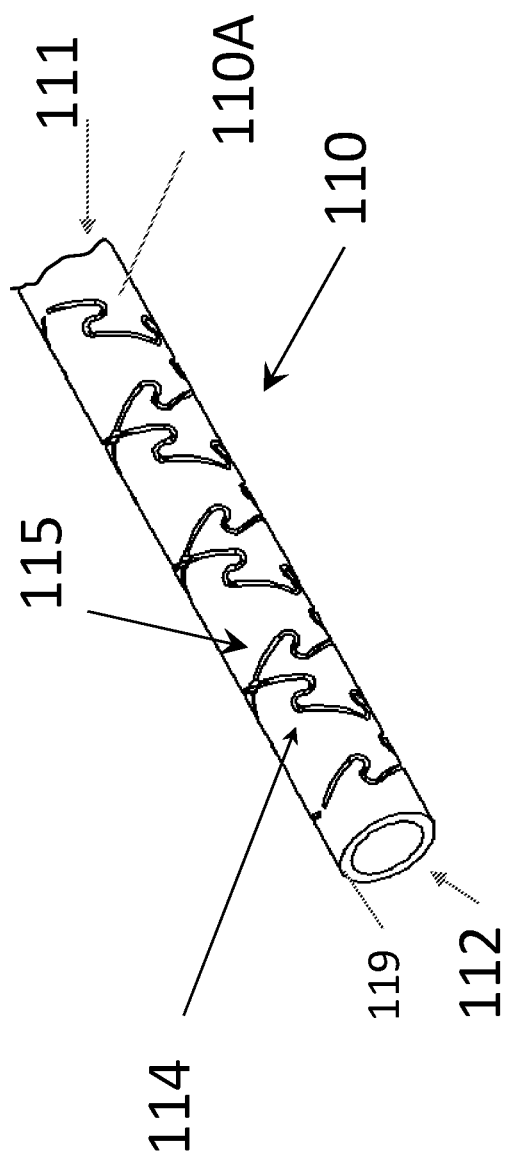
FIG. 20 is an illustration of an intersecting, double helix pattern with a clockwise and counter-clockwise sinuous helical slot in accordance with the invention.

FIG. 20 illustrates a segment of flexible spinal element 110 with a near or proximal end 112 and a far or distal end 111, having a counter-clockwise sinuous helical slot 114 and an intersecting clockwise sinuous helical slot 115 cut into the wall 119. In most applications a second segment would be used extending from either the proximal end 112 or distal end 111. The attachment segment in this figure has been eliminated for illustration purposes and the proximal end 112 can extend further or alternatively the appropriate attachment member can be placed over the slots.

FIG. 21 illustrates the helical angle of the counterclockwise helical slot 114 and clockwise helical slot 115 as φ and β, respectively, starting at the near or proximal end 112 and extending to the far or distal segment end 111. The helical angle of the slots 114 and 115 can range from about 30 degrees to about 85 degrees the ratio of the amplitude of sinuous path to the pitch of the slot is in the range from greater than about 0.1 to about 0.8. The helical angles φ and β, preferably being from 45 to 75 degrees, can be equal or different as the degree of desired flexibility will dictate the respective angles.

FIG. 22 is a horizontal view of the flexible spinal element 110 with intersecting slots 114 and 115 extending through the wall 119 into the internal cavity 123. Detail of the area B is illustrated in FIG. 23.

FIG. 24, is a close up of detail C in FIG. 23 showing the interlocking teeth 117 and 118 created by the slot 114 with a gap 116 and is representative of all slots.

Figure 25:
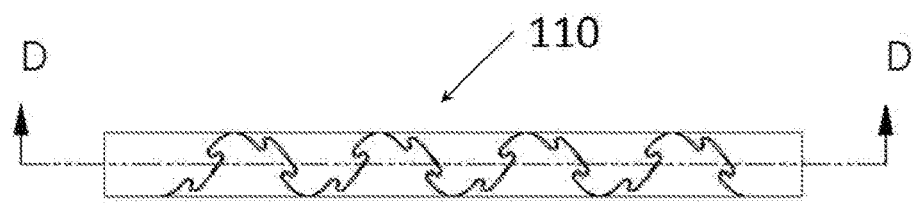
FIG. 25 is the horizontal view of the double helix pattern flexible shaft in FIG. 21 showing the orientation for Section D-D.
Figure 26:
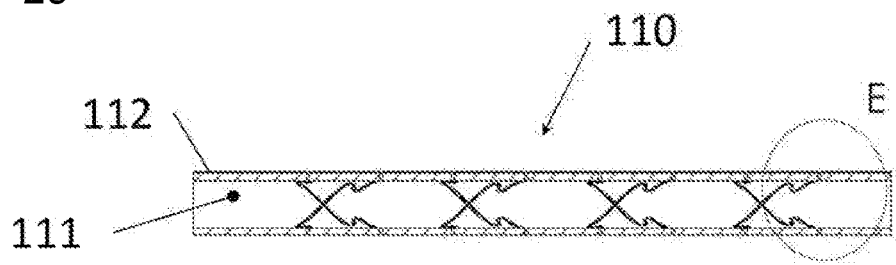
FIG. 26 is a sectional illustration though the longitudinal axis D-D of the central segment in FIG. 25.

FIG. 25 a horizontal view of flexible spinal element 110 showing the location of Section D-D about the central axis of flexible spinal element 110. The sectional view D-D of flexible spinal element 110 in FIG. 26 illustrates the interior cavity of the flexible spinal element 123 and the location of the detailed area E.

Figure 27:
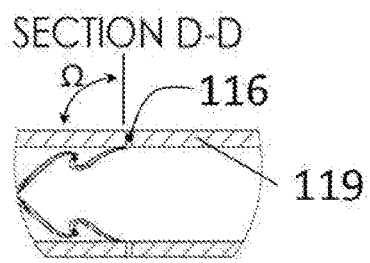
FIG. 27 is a magnified view of the area E in FIG. 26 in accordance with the invention.

FIG. 27 is the detail view of Detail E illustrating the slot angle Ω of the slot gap 116 cut through the wall 119 relative to the longitudinal surface of the flexible spinal element 110. The slot angle would generally be in the range of 0 degrees to 45 degrees (+45 degrees from the normal).

Figure 28:
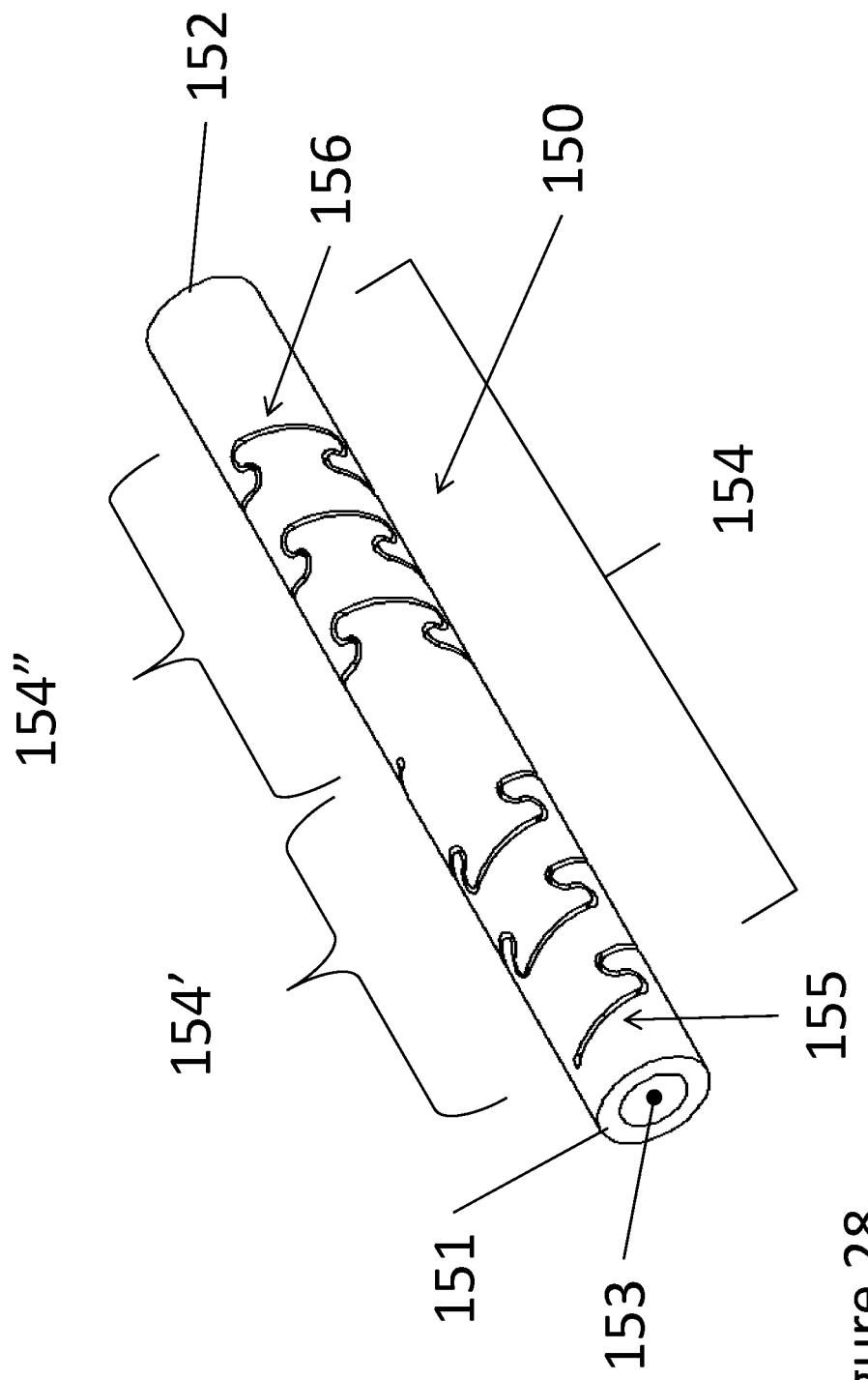
FIG. 28 is an illustration of a multiple helix pattern with a clockwise flexible segment and a counter-clockwise flexible segment in accordance with the invention.

In another embodiment of the invention, as illustrated in FIG. 28, a double slot segment, opposite helix flexible spinal element 150 has an internal cavity 153, near end 151, far end 152, and a flexible segment 154 which contains two or more areas of flexibility 154' and 154" having sinuous helical slots 155 and 156, respectively. The rotation of the slots are such that the general helical rotation of one flexible area is generally in the counter-clockwise orientation while another slot orientation is in the clockwise rotation.

This configuration can be used in a single segment, as illustrated, with securing segments placed at the near end 151 and far end 152 or as a flexible spinal unit with the flexible segment duplicated at either the near end 151 or far end 152 in order to span two vertebra. When used as a two segment unit, a mid-point securing segment would normally be used.

Figures 29, 30:
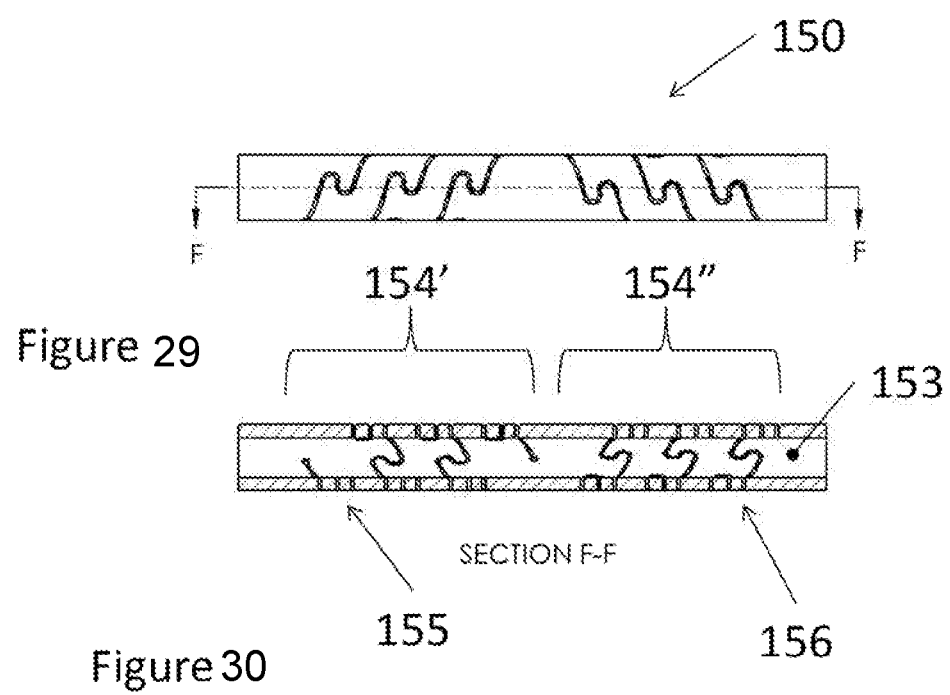
FIG. 29 is the horizontal view of the multiple helix pattern flexible shaft in FIG. 28 showing the orientation for Section F-F.
FIG. 30 is a sectional illustration though the longitudinal axis F-F in FIG. 29.

FIG. 29 shows a horizontal view of the flexible spinal element 150 illustrated in FIG. 28 and the location of section F-F for illustration in FIG. 30.

Figure 31:
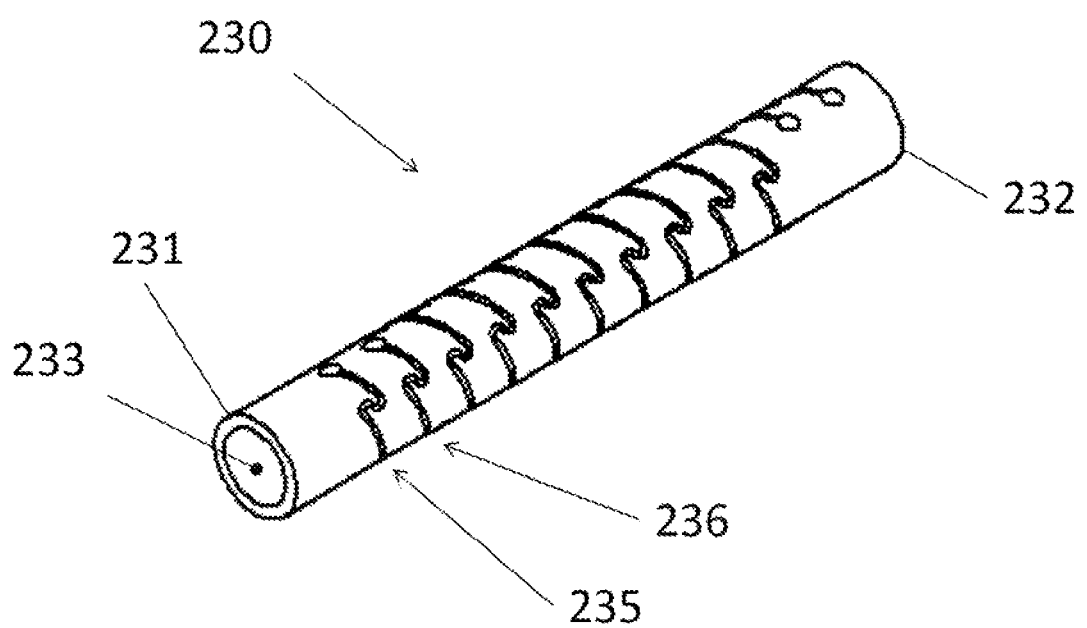
FIG. 31 is an illustration of a multiple helix pattern, flexible segment in accordance with the invention.

FIG. 31 illustrates an additional embodiment of the invention whereby there are two or more serpentine, sinuous helical slots in the flexible spinal element 230 segment with an internal cavity 233, proximal end 231, distal end 232 and a the flexible segment between the two ends which contains two or more sinuous helical slots 235 and 236, preferably in the same rotational direction. The characteristics described previously with regard to slot pattern design, number of slot pattern cycles per revolutions, slot amplitude, slot width, slot undercut and element filler or encapsulation can be the same for both, or multiple slots or they can be different to change the flexibility characteristics of the device.

Figure 32:
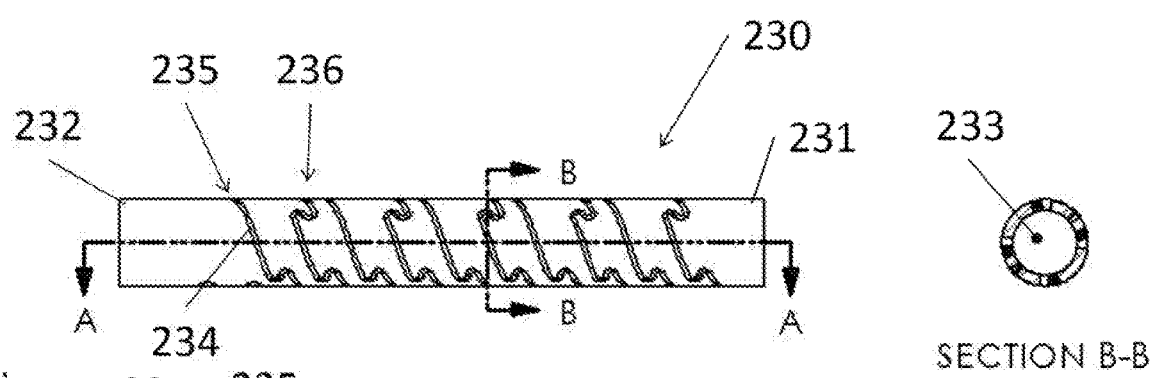
FIG. 32 is the sectional view A-A of the multiple helix pattern flexible shaft in FIG. 31 in accordance with the invention.

FIG. 32 illustrates the horizontal projection of the flexible spinal element 230 and the location of Sections A-A and B-B. In this embodiment there is a difference in the slot configuration for slot 235 as opposed to 236. Slot 235 has an extended non-sinuous helical portion 234 compared to slot 236. The sinuous pattern for any of the slots may be a repeating pattern or could be a random pattern about the helical path and they do not necessarily have to be the same for any or all slots.

Figure 33:
FIG. 33 is a cross sectional illustration though the longitudinal axis B-B in FIG. 32 in accordance with the invention.

FIG. 33 illustrates the cross section B-B of the flexible spinal element 230 to show the open internal cavity 233 that could be filled with a polymer or other flexible material. As previously described the embodiment of the flexible section or sections have a flexible segment that has at least one helical, sinuous slot within a section of the element that is embedded within a polymer or other flexible material so as to fill the slot with the flexible material.

Figure 34:
FIG. 34 is the longitudinal cross section A-A in FIG. 32 in accordance with the invention.

As noted heretofore, in order to reduce the stress concentration effect at the ends of the sinuous slots, larger diameter holes are placed at the ends of the slots. Illustrated in FIG. 34 are near first slot hole 237 and far first slot hole 237' drilled at the end of slot 235 and far second slot hole 238 and near second slot hole 238' drilled at the ends of slot 236.

Figure 35:
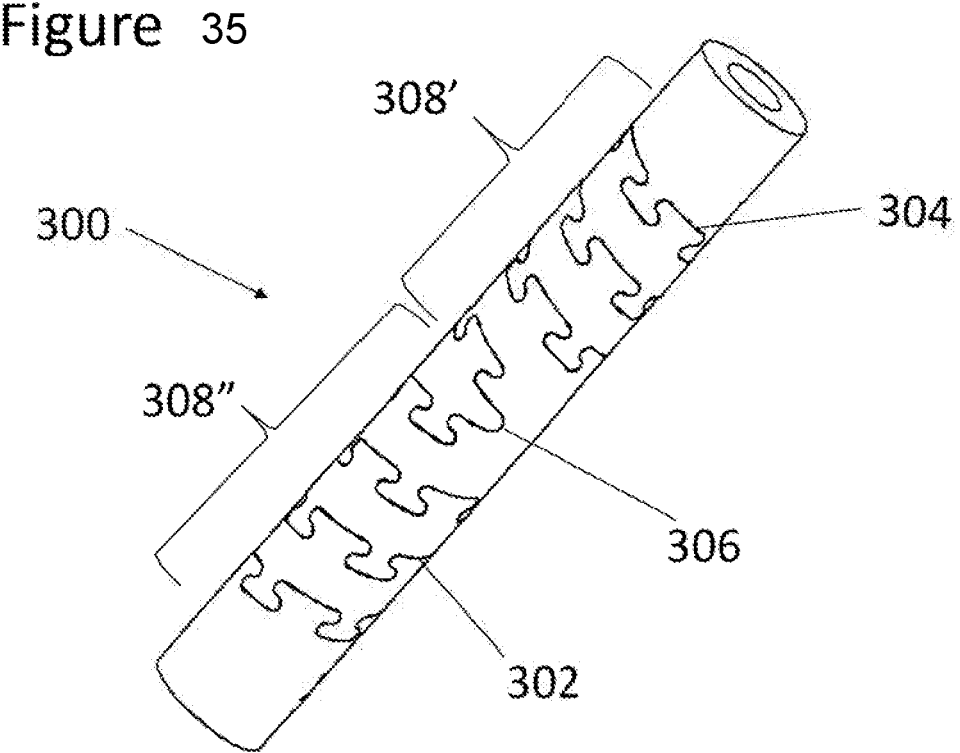
FIG. 35 illustrates the flexible spinal element having two contiguous slots reversing direction without a rigid divider in accordance with the invention.

In FIG. 35 the flexible spinal element 300 segment has proximal slot 302 and distal slot 304 cut contiguously, changing directions at the turning point 306. Thus the two segments 308' and 308" are adjacent to, and contiguous with, one another. The change in direction without a rigid portion between the segments can, depending on the flexible spinal element thickness, slot width, etc., weaken the integrity of the flexible spinal element 300. However, in applications where the contiguous nature of the segments is advantageous, those skilled in the art can, in conjunction with the teachings herein, determine the appropriate ratios.

Figure 36:
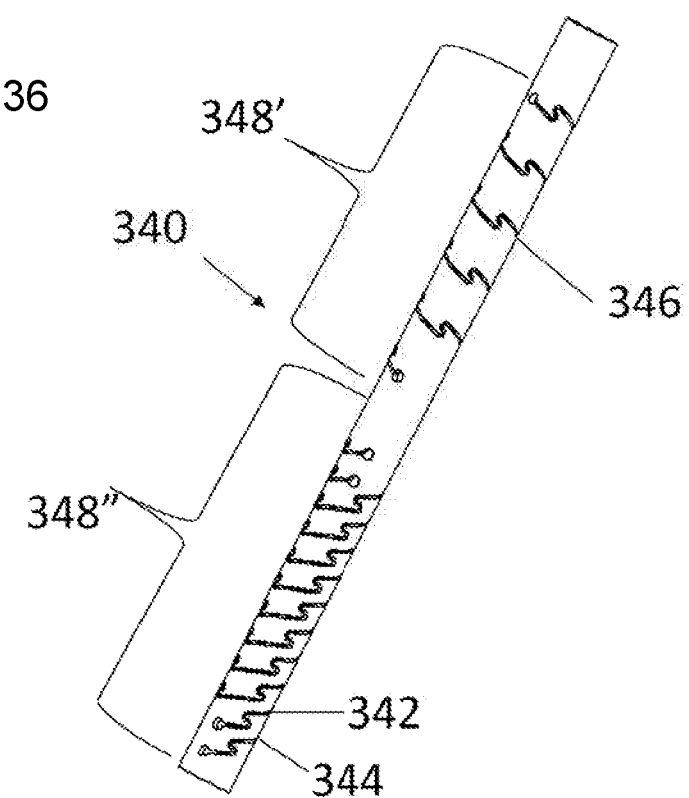
FIG. 36 illustrates a shaft having a double, parallel slot in one segment and a single slot in a second segment, in accordance with the invention.
Figure 38A:
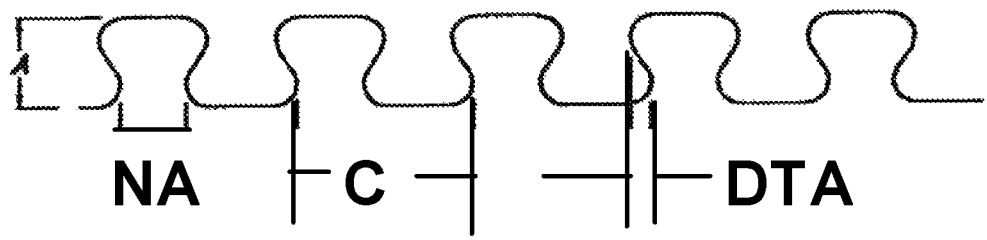
Figure 38B:
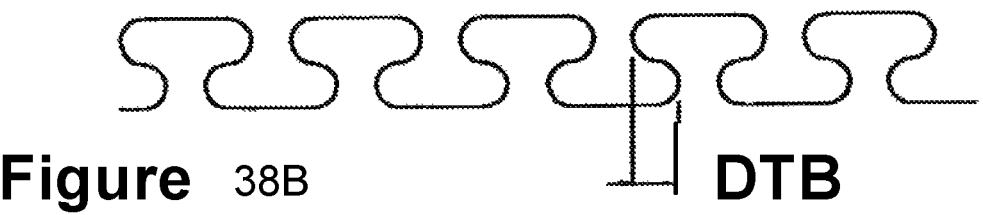
Figure 38C:
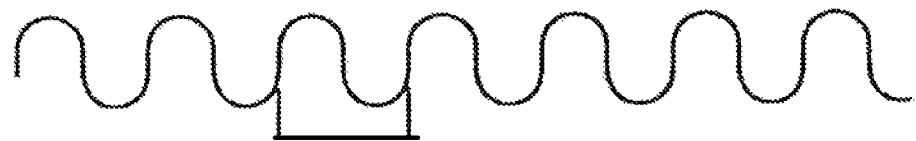
Figure 38D:
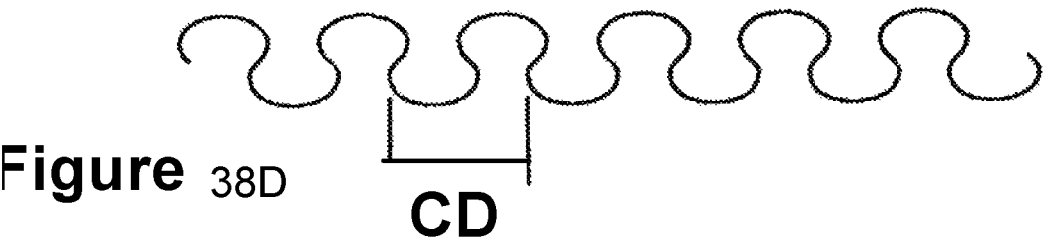
Figure 38E:
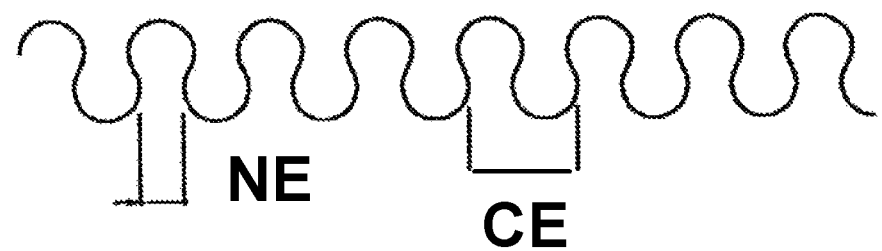
Figure 38F:

In FIG. 36 the flexible spinal element 340 segment is illustrated with parallel first proximal slot 342 and second proximal slot 344 in a first flexible segment 348 and a single slot 346 in distal flexible segment 348'. Another combination of slots is illustrated in FIG. 37 wherein the proximal segment 368" has a sinuous slot 264 ascending in a first direction and sinuous slot 362 ascending in a second direction while the second segment 368' has a single sinuous slot 366.

A variety of slot patterns are illustrated in FIG. 38 A-F. The patterns are representative of patterns that can be used and are not intended to be all inclusive. As illustrated in FIG. 38A, the pattern has a cycle length C, which includes a neck region NA. The wider the neck region the greater the strength of the connector, that is, the greater the torsional forces which the flexible element can transmit. The ability of the device to interlock is dependent in part upon the amount of overlap or dovetailing, indicated as DTA for FIG. 38A and DTB for FIG. 38B. The pattern of 38C, does not provide dovetailing, and requires a helix angle that is relatively small. Additional patterns, as shown in FIGS. 38D, 38E, 38F, can have a configuration as illustrated in U.S. Pat. Nos. 6,053,922 and 6,447,518, the disclosure of which is incorporated herein by reference, as though recited in detail.

Broad Scope of the Invention

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims (e.g., including that to be later added) are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited. In this disclosure and during the prosecution of this application, the terminology "present invention" or "invention" may be used as a reference to one or more aspect within the present disclosure. The language of the present invention or inventions should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features. In this disclosure, the following abbreviated terminology may be employed: "e.g." which means "for example."

What is claimed is:

1. A spine stabilization system for attachment to vertebral bodies to restore or maintain vertebral motion and provide support to the spinal column comprising an elongated spinal element comprising:
    an outer surface diameter,
    an inner cavity having a surface,
        a longitudinal surface,
        multiple segments along said longitudinal surface, said
            multiple segments comprising:
            a distal attachment segment, said distal attachment
                segment dimensioned to be received by a securing
                member configured for attachment to a vertebra;

a proximal attachment segment said proximal attachment segment dimensioned to be received by a securing member configured for attachment to a vertebra;

a rigid center segment, said rigid center segment having a proximal end and a distal end;

a first flexible segment having a first length, said first length extending from a first flexible proximal end adjacent said proximal attachment segment to a first flexible distal end adjacent said proximal end of said rigid center segment; and a second flexible segment having a second length, said second length extending from a second flexible proximal end adjacent said distal end of said rigid center segment to a second flexible distal end adjacent said distal attachment segment; and at least two sinuous slots, a first of said at least two sinuous slots ascending in a helical pattern from a first slot start point at said first flexible proximal end along said first length of said first flexible segment to a first slot end point at said first flexible distal end, and a second of said at least two sinuous slots ascending in a helical pattern from a second slot start point at said second flexible proximal end along said second length of said second flexible segment to a second slot end point at said second flexible distal end, each of said at least two sinuous slots forming interlocking teeth within said longitudinal surface, and each of said at least two sinuous slots having a predetermined configuration, features of said configuration comprising:

a width, a depth from said outer surface diameter to said inner cavity surface, a predetermined rotational direction, and a helical angle;

wherein said first of said at least two sinuous slots has a first configuration and said second of said at least two sinuous slots has a second configuration, said first configuration and said second configuration being individually determined by said features for each of said at least two sinuous slots to enable predetermined independent flexibility within each of said first flexible segment and said second flexible segment, and wherein changing said features for each of said at least two sinuous slots independently changes the flex within of said first flexible segment and said second flexible segment.

2. The spinal stabilization system of claim 1, further comprising an elastomeric material, said elastomeric material applied to at least one from the group of said inner cavity, said at least two sinuous slots, said longitudinal surface, and said surface of said inner cavity.

3. The spinal stabilization system of claim 1 further comprising a third slot, said third slot ascending said length of said first flexible segment in a helical path in a second rotational direction from a third slot start point at said first flexible proximal end to a third slot end point at said first flexible distal end, said first slot start point and said third slot start point being spaced from one another and said first slot end point and said third slot end point being spaced from one another, wherein said first slot and said third slot cross sinuous paths and each of said first slot and said third slot have individual, predetermined features.

4. The spinal stabilization system of claim 3, further comprising a fourth slot, said fourth slot ascending said length of said second flexible segment in a helical path in a second rotational direction from a fourth slot start point at said second flexible proximal end to a fourth slot end point at said second flexible distal end, said second slot start point and said fourth slot start point being spaced from one another and said second slot end point and said fourth slot end point being spaced from one another, wherein said second slot and said fourth slot cross sinuous paths and each of said second slot and said fourth slot have individual, predetermined features.

5. The spinal stabilization system of claim 1, further comprising a third slot, said third slot ascending said length of said first flexible segment in a helical path in said first rotational direction from a third slot start point at said first flexible proximal end to a third slot end point at said first flexible distal end, said first slot start point being spaced from said third slot start point and said first slot end point being spaced from said third slot end point, wherein said first slot and said third slot have parallel, spaced, ascending paths and each of said first slot and said third slot have individual, predetermined features.

6. The spinal stabilization system of claim 5, further comprising a fourth slot, said fourth slot ascending said length of said second flexible segment in a helical path in said first rotational direction from a fourth slot start point at said second flexible proximal end to a fourth slot end point at said second flexible distal end, said second slot start point and said fourth slot start point being spaced from one another and said second slot end point and said fourth slot end point being spaced from one another, wherein said second slot and said fourth slot have parallel, spaced, ascending paths and each of said second slot and said fourth slot have individual, predetermined features.

7. The spinal stabilization system of claim 1, wherein each of said at least two sinuous slots within each of said first flexible segment and said second flexible segment has a configuration selected from a group comprising: single sinuous slot first rotational direction, single sinuous slot second rotational direction, a single sinuous slot first longitudinal direction, a single sinuous slot second longitudinal direction, multiple sinuous slots first rotational direction, and multiple sinuous slots in a first rotational direction and a second rotational direction.

8. The spine stabilization system of claim 1, wherein each of said at least two sinuous slots has a width between 2.5% and 10% of said diameter of said spinal element.

9. The spinal stabilization system of claim 1, wherein each of said at least two sinuous slots has an angle from about 5 degrees to about 20 degrees.

10. The spinal stabilization system of claim 1, wherein each of said at least two sinuous slots has a ratio of amplitude to pitch in the range of from greater than 0.1 to about 0.8.

11. The spinal stabilization system of claim 1, wherein each of said at least two sinuous slots has about 4-6 cycles per diameter length.

12. The spinal stabilization system of claim 1 further comprising:

a. a third slot, said third slot ascending said length of said first flexible segment in a helical path in a second rotational direction from a third slot start point at said first flexible proximal end to a third slot end point at said first flexible distal end, said first slot start point and said third slot start point being spaced from one another and said first slot end point and said third slot end point being spaced from one another, wherein said first slot and said third slot cross sinuous paths and each of said first slot and said third slot have individual, predetermined features, and b. a fourth slot, said fourth slot ascending said length of said second flexible segment in a helical path in a second rotational direction from a fourth slot start point at said second flexible proximal end to a fourth slot end point at said second flexible distal end, said second slot start point and said fourth slot start point being spaced from one another and said second slot end point and said fourth slot end point being spaced from one another, wherein said second slot and said fourth slot cross sinuous paths and each of said second slot and said fourth slot have individual, predetermined features.

13. The spinal stabilization system of claim 1, further comprising:

a. a third slot, said third slot ascending said length of said first flexible segment in a helical path in said first rotational direction from a third slot start point at said first flexible proximal end to a third slot end point at said first flexible distal end, said first slot start point being spaced from said third slot start point and said first slot end point being spaced from said third slot end point, wherein said first slot and said third slot have parallel, spaced, ascending paths and each of said first slot and said third slot have individual, predetermined features, and b. a fourth slot, said fourth slot ascending said length of said second flexible segment in a helical path in said first rotational direction from a fourth slot start point at said second flexible proximal end to a fourth slot end point at said second flexible distal end, said second slot start point and said fourth slot start point being spaced from one another and said second slot end point and said fourth slot end point being spaced from one another, wherein said second slot and said fourth slot have parallel, spaced, ascending paths and each of said second slot and said fourth slot have individual, predetermined features.

14. The spinal stabilization system of claim 1 further comprising:

a. a third slot, said third slot ascending said length of said first flexible segment in a helical path in a second rotational direction from a third slot start point at said first flexible proximal end to a third slot end point at said first flexible distal end, said first slot start point and said third slot start point being spaced from one another and said first slot end point and said third slot end point being spaced from one another, wherein said first slot and said third slot cross sinuous paths and each of said first slot and said third slot have individual, predetermined features, and a fourth slot, said fourth slot ascending said length of said second flexible segment in a helical path in said first rotational direction from a fourth slot start point at said second flexible proximal end to a fourth slot end point at said second flexible distal end, said second slot start point and said fourth slot start point being spaced from one another and said second slot end point and said fourth slot end point being spaced from one another, wherein said second slot and said fourth slot have parallel, spaced, ascending paths and each of said second slot and said fourth slot have individual, predetermined features.

15. A spine stabilization system for attachment to vertebral bodies to restore or maintain vertebral motion and provide support to the spinal column comprising an elongated spinal element comprising:

an outer surface diameter;

an inner cavity having a surface;

a longitudinal surface having a tube proximal end and a tube distal end;

multiple segments along said longitudinal surface, each of said multiple segments having a segment proximal end and a segment distal end, said multiple segments comprising:

a distal attachment segment, said distal attachment segment dimensioned to be received by a securing member configured for attachment to a vertebra;

a proximal attachment segment, said proximal attachment segment dimensioned to be received by a securing member configured for attachment to a vertebra;

a rigid center segment having a proximal end and a distal end and dimensioned to be received by a securing member configured for attachment to a vertebra;

a first flexible segment having a length extending from a first flex flexible proximal end adjacent said proximal attachment segment to a first flex flexible distal end adjacent said proximal end of said rigid center segment; and a second flexible segment having a length extending from a second flexible proximal end adjacent said distal attachment segment to a second flexible distal end adjacent said distal end of said rigid center segment; and at least two sinuous slots within said longitudinal surface of said elongated spinal element, said at least two sinuous slots extending said length of at least one of said first flexible segment and said second flexible segment, each of said at least two sinuous slots having a predetermined configuration, features of said configuration comprising:

a width between 2.5% and 10% of said surface diameter, a depth from said longitudinal surface to said inner cavity, a slot start point at one end of each of said at least two slots, a slot end point at a second end of each of said at least two slots, a rotational direction, an angle from about 5 degrees to about 20 degrees, a ratio of amplitude to pitch in the range of from greater than 0.1 to about 0.8, and 4-6 cycles per diameter length, wherein each of said at least two sinuous slots has an individual configuration, said configuration being determined by said features of said at least two sinuous slots to enable independent, predetermined flexibility within each of said first flexible segment and said second flexible segment, and wherein changing said features changes said configuration to change the flex within said first flexible segment and said second flexible segment.

* * * * *